United States Patent
Fujieda et al.

(10) Patent No.: US 10,265,678 B2
(45) Date of Patent: Apr. 23, 2019

(54) POROUS FIBERS, ADSORBENT MATERIAL, AND PURIFICATION COLUMN

(71) Applicant: TORAY INDUSTRIES, INC., Tokyo (JP)

(72) Inventors: Hiroaki Fujieda, Otsu (JP); Yoshiyuki Ueno, Otsu (JP); Kazumi Tanaka, Otsu (JP)

(73) Assignee: TORAY INDUSTRIES, INC. (JP)

( * ) Notice: Subject to any disclaimer, the term of this patent is extended or adjusted under 35 U.S.C. 154(b) by 0 days.

(21) Appl. No.: 15/521,469

(22) PCT Filed: Oct. 20, 2015

(86) PCT No.: PCT/JP2015/079542
§ 371 (c)(1),
(2) Date: Apr. 24, 2017

(87) PCT Pub. No.: WO2016/067967
PCT Pub. Date: May 6, 2016

(65) Prior Publication Data
US 2017/0333871 A1 Nov. 23, 2017

(30) Foreign Application Priority Data
Oct. 28, 2014 (JP) .................. 2014-219036

(51) Int. Cl.
*B01J 20/28* (2006.01)
*B01J 20/26* (2006.01)
(Continued)

(52) U.S. Cl.
CPC ...... *B01J 20/28023* (2013.01); *A61M 1/3679* (2013.01); *B01D 15/206* (2013.01);
(Continued)

(58) Field of Classification Search
CPC . A61M 1/1672; A61M 1/3679; B01D 15/206; B01J 20/261; B01J 20/28023;
(Continued)

(56) References Cited

U.S. PATENT DOCUMENTS 9,511,529 B2  12/2016 Fujimura et al.
2014/0364307 A1  12/2014 Onohara et al.

FOREIGN PATENT DOCUMENTS

JP   58169510 A   10/1983
JP   05148709 A   6/1993
(Continued)

OTHER PUBLICATIONS

English translation Japanese Patent Application No. H06 296860 A (1994).*
(Continued)

*Primary Examiner* — John Kim
(74) *Attorney, Agent, or Firm* — RatnerPrestia

(57) ABSTRACT

There are provided porous fibers having excellent removal performance with respect to a material to be purified; and a purification column into which an adsorbent material obtained by bundling the fibers is incorporated. The porous fibers satisfying the following conditions (a) and (b) and having a shape in which three or more projected parts are continuously present in the lengthwise direction on the periphery part of a solid-state fiber: (a) The modification degree Do/Di in a cross section is 1.2 to 6.6 when the diameter of the inscribed circle is denoted by Di and the diameter of the circumscribed circle is denoted by Do., and (b) The specific surface area of pores is 50 m²/g or more.

17 Claims, 10 Drawing Sheets

(51) Int. Cl.
*B01J 20/30* (2006.01)
*A61M 1/36* (2006.01)
*B01D 15/20* (2006.01)
*D01F 6/00* (2006.01)
*A61M 1/16* (2006.01)

(52) U.S. Cl.
CPC .............. *B01J 20/26* (2013.01); *B01J 20/261* (2013.01); *B01J 20/28* (2013.01); *B01J 20/28011* (2013.01); *B01J 20/28052* (2013.01); *B01J 20/28059* (2013.01); *B01J 20/28078* (2013.01); *B01J 20/3007* (2013.01); *D01F 6/00* (2013.01); *A61M 1/1672* (2014.02); *D10B 2401/10* (2013.01)

(58) Field of Classification Search
CPC ............ B01J 20/28052; B01J 20/28059; B01J 20/3007; B01J 20/26; B01J 20/28; B01J 20/28078; B01J 20/28011; D01F 6/00; D10B 2401/10
See application file for complete search history.

(56) References Cited

FOREIGN PATENT DOCUMENTS

| | | |
|---|---|---|
| JP | H06 296860 A * | 10/1994 |
| JP | 07171360 A | 7/1995 |
| JP | 10251915 A | 9/1998 |
| JP | 1136272 A | 2/1999 |
| JP | 11179174 A | 7/1999 |
| JP | 11292133 A | 10/1999 |
| JP | 2006000810 A | 1/2006 |
| JP | 2010148851 A | 7/2010 |
| JP | 2010188253 A | 9/2010 |
| JP | 2011156022 A | 8/2011 |
| WO | 2011129023 A | 10/2011 |
| WO | 2013111857 A | 5/2015 |

OTHER PUBLICATIONS

International Search Report and Written Opinion for International Application No. PCT/JP2015/079542, dated Jan. 26, 2016, 6 Pages.

* cited by examiner

[Fig. 1]
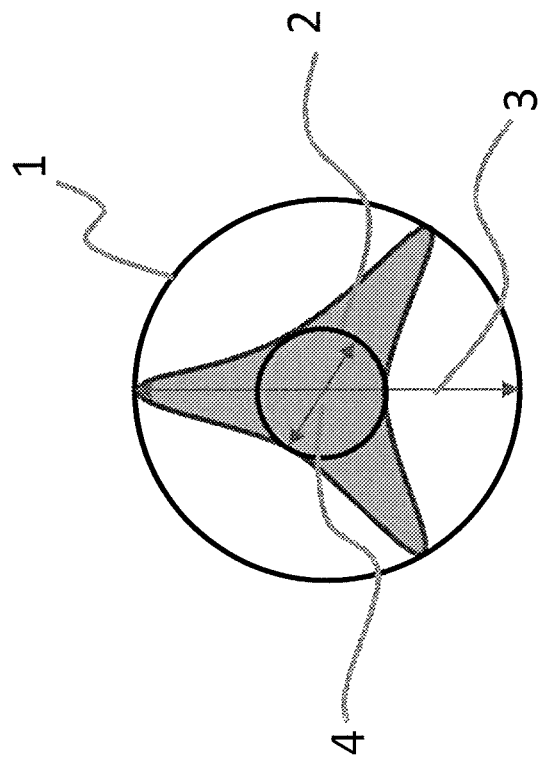

[Fig.2]
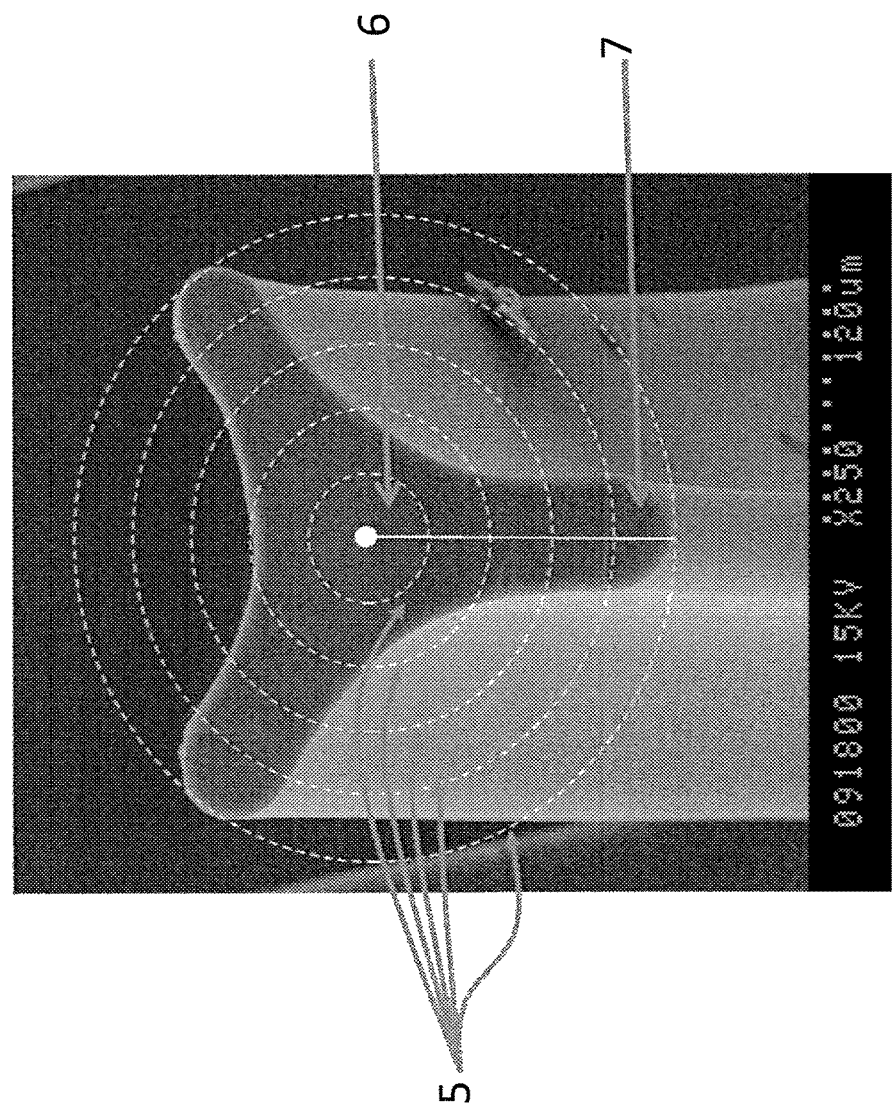

[Fig. 3]
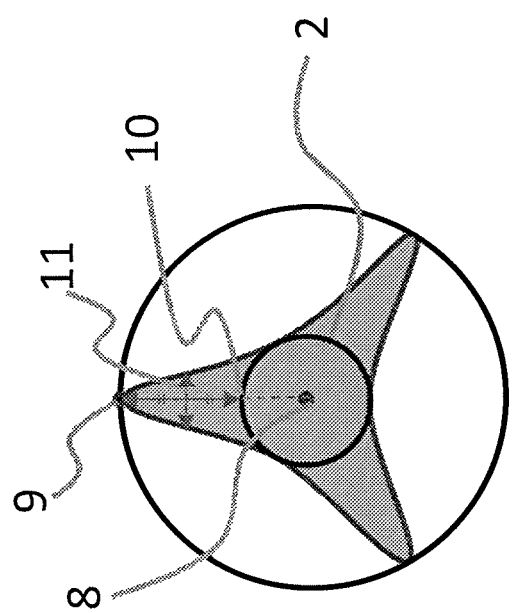

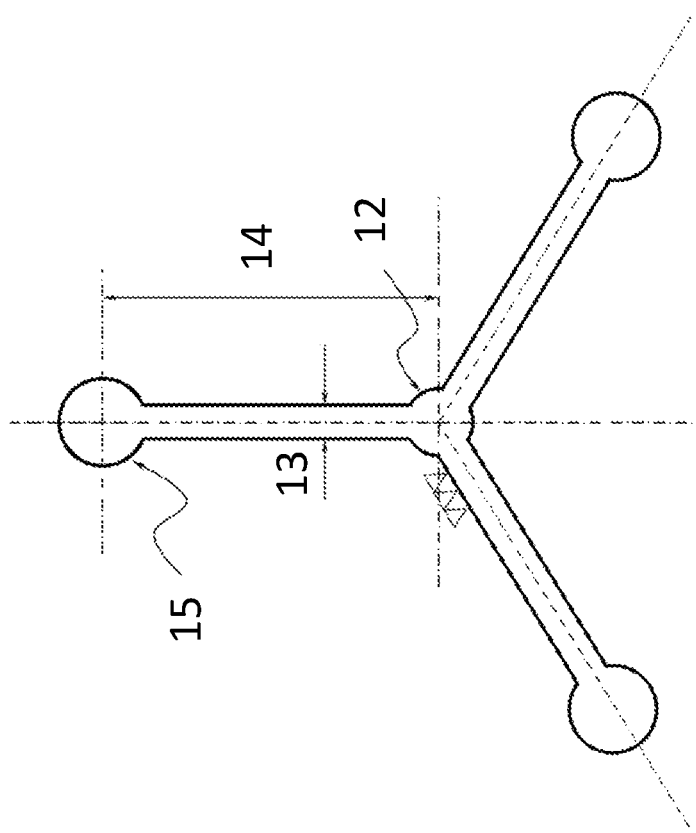
[Fig.4]

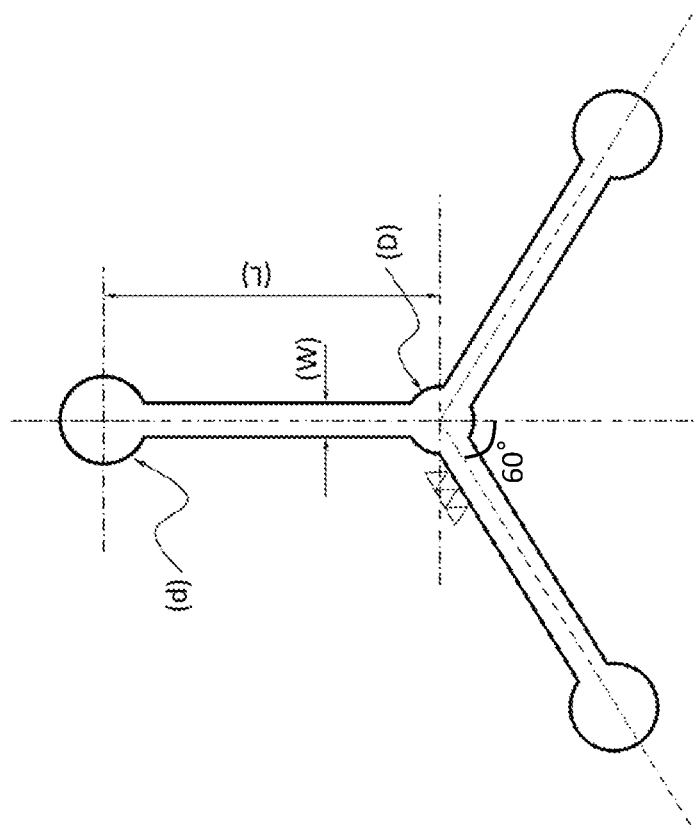
[Fig.5]

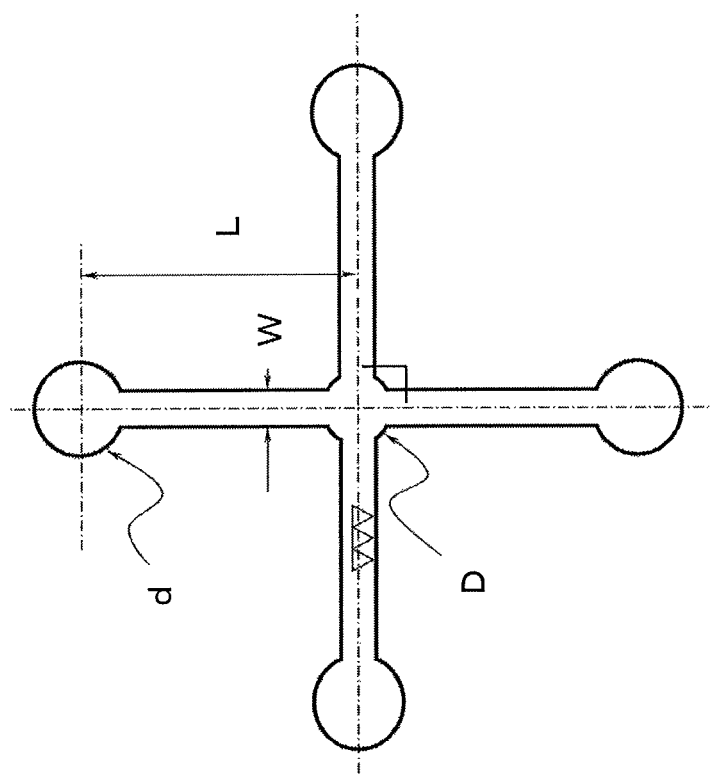
[Fig.6]

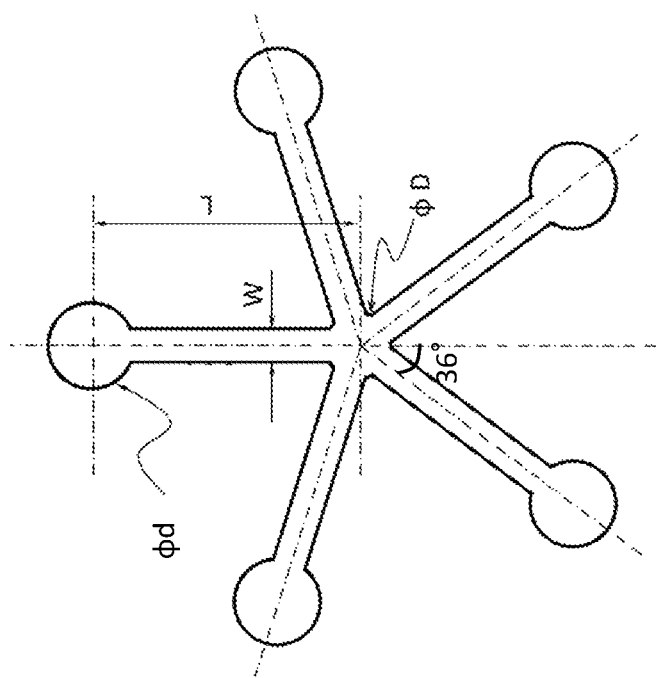
[Fig.7]

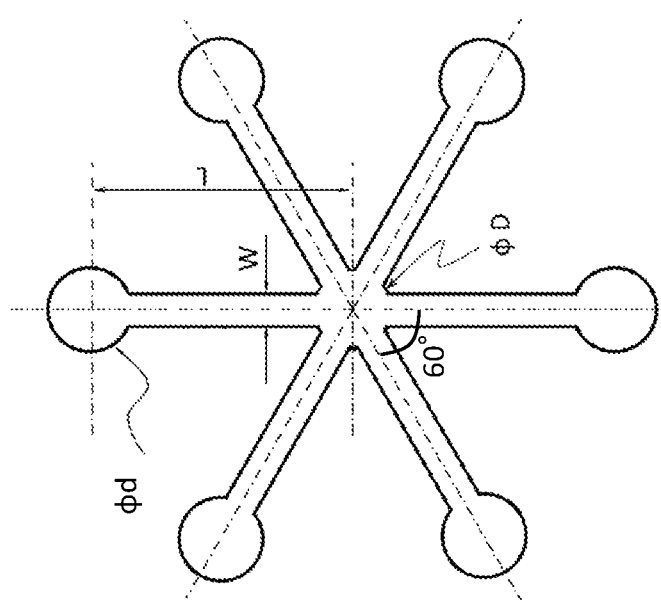
[Fig.8]

[Fig.9]
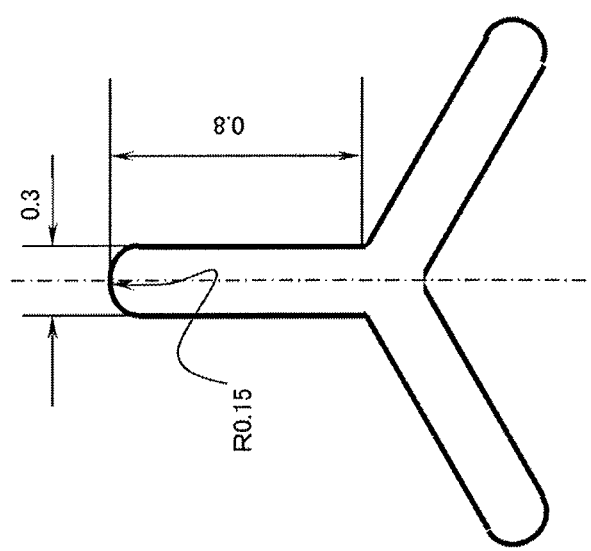

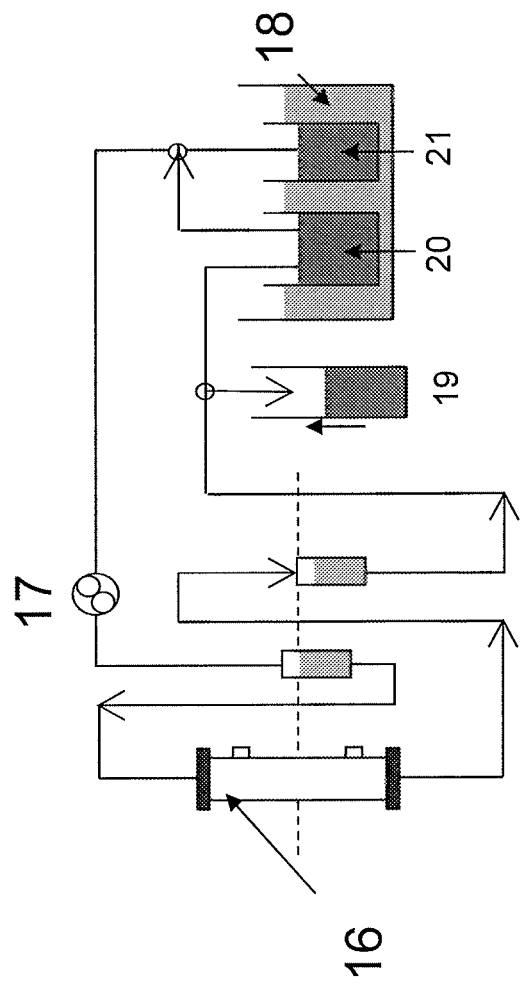
[Fig.10]

POROUS FIBERS, ADSORBENT MATERIAL, AND PURIFICATION COLUMN

CROSS REFERENCE TO RELATED APPLICATIONS

This is the U.S. National Phase application of PCT/JP2015/079542, filed Oct. 20, 2015, and claims priority to Japanese Patent Application No. 2014-219036, filed Oct. 28, 2014, the disclosures of each of these applications being incorporated herein by reference in their entireties for all purposes.

FIELD OF THE INVENTION

The present invention relates to porous fibers. Particularly, it relates to porous fibers which can adsorb a removal-object substance in the fluid that is to be treated with efficiency, an adsorbent material formed by using the porous fibers as a bundle, and a purification column into which the porous fibers are incorporated.

BACKGROUND OF THE INVENTION

Conventionally, porous beads are often used as the form of the adsorbent material to be used for the purification column which removes, by adsorption, a removal-object substance in the fluid that is to be treated. Examples of the reasons for this include the fact that bead-shaped adsorbent has advantages of less unbalanced blood flow in a column and hence ease of a column design because the adsorbent can be uniformly packed into an adsorption column. On the other hand, examples of a means for improving adsorption performance include increasing of a surface area per volume of the adsorbent. However, when the adsorbent is bead-like, a bead diameter is decreased in order to increase a surface area per volume of the adsorbent, a gap between the beads becomes narrow. Therefore, since resistance of a flow path becomes high to increase a pressure loss, it becomes difficult to pass the fluid that is to be treated. Further, the bead used as an adsorbent is usually spherical, and therefore it has a disadvantage that the surface area per volume is inherently small. That is, even though there is an adsorption reserve capacity inside the bead, an internal adsorption site cannot be effectively used.

Examples of the form of an adsorbent material other than the bead include a fiber, it is also thought to use a fiber having a common circular cross section. Examples of the form of the fiber include one obtained by inserting a large number of fibers in the straight form in parallel to a lengthwise direction of a column case, or one obtained by forming a knitting fabric.

In the knitting fabric of these forms, it is difficult in production to make the fiber porous for providing adsorption holes for the fiber. Further, when the fluid that is to be treated includes many dissolved substances and viscosity is high, it is not so preferred since processing easily results in a pressure rise in a column.

On the other hand, the fiber of the form obtained by inserting filament fibers such as a solid-state fiber or a hollow fiber in the straight form in parallel to a lengthwise direction of a column case, can secure a flow path of the fluid that is to be treated separately from the adsorbent material. Therefore, the fiber of this form can suppress resistance of the flow path, and is advantageous to the adhesion of a dissolved substance in the fluid that is to be treated. Hitherto, the inventions concerning a purification column into which hollow fibers or solid-state fibers are incorporated are disclosed (Patent Documents 1 and 2). However, a cross-section shape of the fibers used in these documents is circular, and the adsorption performance has been low since the surface area per volume of the adsorbent is small.

Here, a method in which a shape other than a circular shape is used as a cross-section shape of the fiber, that is, a fiber with a modified cross section is used, is known. However, it is heretofore thought that since spinning stability deteriorates when the modification degree of the fiber is increased, an increase of the modification degree is suppressed. Particularly, in the case of the porous fibers, there has been a fear that strength-elongation of the fiber is significantly reduced and unevenness of a fiber diameter referred to as draw resonance increases by a modified cross section, and in addition to this, there has been a fear that modification of a cross-section shape, particularly, agglutination of the projected part within a single fiber cross section, occurs.

However, heretofore, Patent Documents 3 to 5 describe the invention concerning the fibers with the modified cross section in which a shape other than a circular shape is used as a cross-section shape of the porous fiber. However, these fibers differ from aspects of the present invention in that all of the fibers pertain to a separation membrane of a hollow fiber type. In the case of the hollow fiber, modification of a cross-section shape described above hardly occurs since fixation of a structure can be performed at the same time from both side of the inside of a fiber (hollow portion) and the outside of a fiber in forming a fiber (=spinning). The fixation of a structure is performed through cooling by cool wind or through contact with a poor (non) solvent. Therefore, the hollow fiber is more advantageous than the solid-state fiber which can be cooled only from the outside of the fiber. As results of viewing each of concepts/objects of modifying a fiber shape in Patent Documents described above, prevention of intimate contact between bundles in bundling the fibers (Patent Document 3) and suppressing fouling by complicating and disturbing a flow on an outer surface of a hollow fiber ((Patent Documents 4 and 5) are mainly described. That is, shapes provided with short protrusions on the periphery of a fiber are merely employed for the object different from the present invention. Particularly, the above concept of suppressing fouling is contrary to the concept of an adsorption column which adsorbs a dissolved substance on the fiber. Accordingly, a concept of improving the adsorption performance by increasing a surface area per volume is not present. Therefore, a shape in which the modification degree is less-than-relatively high is shown.

In Patent Document 6, a separation membrane in which a modified cross section is formed is described. However, with respect to its "separation" function, a paragraph [0005] in the specification describes "one of performance indexes as a multilayer composite separation membrane is a permeation rate, and when a membrane material is the same, it is important to decrease a thickness of a separation layer and to increase a membrane area of a separation layer". That is, it is assumed that an object-substance is separated by permeating a membrane. From such a viewpoint, a cross-section shape is modified aiming at an improvement of separation performance by increasing a membrane area of a separation membrane. Accordingly, specifically, a hollow fiber membrane is described, and it cannot be substantially said that a fiber of solid-state form is described.

That is, a technology of modifying a cross-section shape of a hollow fiber which is used in the above document is not a technology designed in consideration of use of a fiber as an adsorbent material.

On the other hand, Patent Document 7 describes the invention concerning the fibers with the modified cross section which has, but not having a hollow portion, pores on the surface. However, in aspects of this invention, pores are provided for splitting a fiber so as to increase a fiber volume and hence small. That is, the pore is largely different in pore size, pore size distribution and pore specific surface area from the pore for adsorption, and it is hard to say that the fiber is a material generally referred to as a porous fiber.

PATENT DOCUMENTS

Patent Document 1: Japanese Patent Laid-open Publication No. 2011-156022
Patent Document 2: Japanese Patent Laid-open Publication No. 2010-148851
Patent Document 3: Japanese Patent Laid-open Publication No. 58-169510
Patent Document 4: WO 2011/129023 A
Patent Document 5: Japanese Patent Laid-open Publication No. 2010-188253
Patent Document 6: Japanese Patent Laid-open Publication No. 7-171360
Patent Document 7: Japanese Patent Laid-open Publication No. 10-251915

NON-PATENT DOCUMENT

Non-patent Document 1: Kazuhiko Ishikiriyama et al.; JOURNAL OF COLLOID AND INTERFACE SCIENCE, 171, 103-111, (1995)

SUMMARY OF THE INVENTION

It is an object of the present invention to provide porous fibers having excellent removal performance with respect to a material to be adsorbed, and a purification column into which an adsorbent material obtained by bundling the fibers is incorporated.

According to investigations of the present inventors, in Patent Documents 3 and 5, a thick dense layer (separation layer) is present in the surface of a fiber, and thereby, an adsorption-object substance cannot reach pores within the fibers resulting in deterioration of the adsorption performance. Further, in such fibers, since it is assumed to use the fibers for separation application, a specific surface area of pores is small. In addition, since the fibers have a structure which is asymmetric in a film thickness direction, a pore size distribution of pores is wide.

In Patent Document 6, pore opening is performed by stretching of a modified cross-section fiber prepared by melt spinning. Accordingly, it is difficult to control a specific surface area of a pore by forming a network structure by many pores. Its microcrack structure is elongated in stretching to form pores having various sizes, and therefore the specific surface area is reduced. Further, since a distribution of a pore size tends to be widen, a pore having a pore size much smaller than the size of the material to be adsorbed cannot contribute to the adsorption. That is, an area, not contributing to the adsorption, of the specific surface area of the pore is partially present. Further, since pore opening is performed by stretching of the fiber, a support material of the fiber is limited to a crystalline polymer.

The present invention aims at solving the above-mentioned problems which the prior art has.

The present inventors made earnest investigations in order to solve the above-mentioned problems, and consequently they found that it is important for improvement of the adsorption performance that porous fibers have a shape in which the porous fibers have three or more projected parts on the periphery part of each fiber and the projected parts are continuous in the lengthwise direction of the fiber.

Furthermore, according to findings in the present invention, in the design of the adsorbent material, it is important not only to increase the surface area per volume of the fiber surface by forming a modified cross section but also to increase the specific surface area of pores within the fiber. The reason for this is that an area of a surface capable of adsorption can be increased by increasing the specific surface area.

That is, the present invention includes the following constitution.

(1) The porous fibers satisfy the following conditions (a) and (b) and have a shape in which three or more projected parts are continuously present in the lengthwise direction on the periphery part of a solid-state fiber.
  (a) When the diameter of the inscribed circle is denoted by Di and the diameter of the circumscribed circle is denoted by Do in a cross section,
     the modification degree Do/Di is 1.2 to 6.6.
  (b) The specific surface area of the pores is 50 m$^2$/g or more.
(2) An adsorbent material formed by using the porous fibers of the above (1) as a bundle.
(3) A purification column which is formed by arranging the adsorbent material described in the above (2) in the straight form in a direction of a case axis in a plastic casing and attaching an inlet port and an outlet port of the fluid that is to be treated to both ends of the casing.

According to the present invention, it is possible to provide porous fibers which can adsorb a removal-object substance in the fluid that is to be treated with efficiency, and a purification column into which the porous fibers are incorporated.

BRIEF DESCRIPTION OF THE DRAWINGS

FIG. 1 is a view showing a fiber cross section for explaining an inscribed circle and a circumscribed circle.
FIG. 2 is a view showing a central region and a near-outer surface region of a cross section.
FIG. 3 is a view for explaining a projected part thickness ω.
FIG. 4 is a view of a spinneret for producing fibers in which the number of its projected parts is three, and a view for explaining each part of a spinneret.
FIG. 5 is a view of a spinneret for producing fibers in which the number of its projected parts is three.
FIG. 6 is a view of a spinneret for producing fibers in which the number of its projected parts is four.
FIG. 7 is a view of a spinneret for producing fibers in which the number of its projected parts is five.
FIG. 8 is a view of a spinneret for producing fibers in which the number of its projected parts is six.
FIG. 9 is a view of a spinneret for producing fibers in which the number of its projected parts is three.
FIG. 10 is a view of a circuit at the time of measuring adsorption performance of a column.

DETAILED DESCRIPTION OF EMBODIMENTS OF THE INVENTION

The porous fibers of the present invention assume a configuration/form of porous fibers not having a hollow portion which are referred to as a solid-state fiber. In the case of the hollow fiber, even if an outer surface of the hollow fiber is formed into a modified cross section and the fluid that is to be treated is brought into contact with only the outside of the hollow fiber, a surface area inside the hollow fiber cannot be effectively used. Further, when the fluid that is to be treated is passed through inside the hollow fiber, the effect of the modified cross section cannot be achieved. Although there is a technique in which the fluid that is to be treated is passed through both inside and outside the hollow fiber, it is difficult to evenly distribute to inside flow and outside flow, and uneven flow tends to occur. For example, an operation in which after blood is passed as a fluid that is to be treated, the blood remaining in the column is returned to the inside of the body using a normal saline (sometimes referred to as "blood reinfusion"), is conducted. However, this is not preferred since there is a fear of the occurrence of a phenomenon referred to as remaining blood in which in the case of a small inner diameter of the hollow fiber, a large amount of blood remains within the hollow fiber in the blood reinfusion.

Further, a plurality of monofilaments of solid-state fibers may be combined to form a multi-filament, but it is not preferred since a tangled portion hardly contacts the fluid that is to be treated and there is a high possibility that the surface area cannot be effectively used for adsorption. The multi-filament referred to herein means a yarn composed of a large number of monofilament. The multi-filament includes both of one composed of the same fibers and one composed of different types of fibers.

The porous fibers according to embodiments of the present invention have a shape in which the porous fibers have three or more projected parts on the periphery part of each fiber and the projected parts are continuously present in the lengthwise direction of the fiber. The projected parts referred to herein are projections which are present on the periphery part of a cross section of each fiber. By having the projected parts, the shape of the fiber is modified to increase the surface area per volume, and consequently an improvement of the adsorption performance can be expected.

An upper limit of the number of the projected parts is preferably 12, still more preferably eight, and particularly preferably six. When the number of the projected parts is too many, it is not preferred since a clearance between the projected parts is narrowed, and therefore the surface area per volume is reduced or the fluid that is to be treated becomes hard to contact the projected part between the projected parts. The modification degree of the porous fibers is represented by a ratio in diameter between an inscribed circle and a circumscribed circle in observing the fiber cross section, that is, a ratio Do/Di between a diameter of the inscribed circle Di and a diameter of the circumscribed circle Do.

Herein, the modified cross section may have a shape retaining symmetry such as symmetry with respect to a line or symmetry with respect to a point or may have an asymmetric shape; however, the modified cross section preferably has a shape having symmetry on the whole from the viewpoint of having uniform fiber properties. When it is determined that the modified cross section retains symmetry with respect to a line or symmetry with respect to a point on the whole, the inscribed circle is a circle inscribed in a curve which forms the outline of a fiber in the fiber cross section, and the circumscribed circle is a circle circumscribing a curve which forms the outline of a fiber in the fiber cross section. A circumscribed circle, an inscribed circle, and diameters Do and Di in the case where fibers with a modified cross section in which the number of the projected parts is three are used, are shown in FIG. 1.

On the other hand, when it is determined that the modified cross section does not retain symmetry with respect to a line or symmetry with respect to a point at all, the inscribed circle and the circumscribed circle are defined as follows. A circle having a maximum radius which is possible in the scope in which a circle is inscribed in a curve which forms the outline of a fiber at least at two points so that the circle is present only inside the fiber and the circumference of the circle does not intersect with the curve, is taken as the inscribed circle. A circle having a minimum radius which is possible in the scope in which a circle circumscribes a curve which forms the outline of a fiber at least at two points so that the circle is present only outside the fiber and the circumference of the circle does not intersect with the curve, is taken as the circumscribed circle.

In any modified shape, if the modification degree is 1.2 or more, it becomes possible to enhance the ability of a fiber to adsorb the removal-object substance. The reason for this is that the surface area per volume is generally increased as the modification degree increases, and therefore the adsorption performance can be improved. Accordingly, a lower limit of the modification degree is preferably 1.2, more preferably 1.5, still more preferably 1.8, and particularly preferably 2.0. On the other hand, when the modification degree is excessively increased, another problem can arise. That is, a central portion of the fiber cross section and the projected part of the fiber cross section are narrow and the strength-elongation of the fiber is reduced, and therefore bending and break of the projected part easily occur to cause a reduction of spinning stability and difficulty of maintaining a fiber shape. Further, when the raw spinning solution not yet formed into a fiber is quickly cooled with use of wind or liquid, the projected part interfere with a flow of the wind or liquid. As a result of this, there is a fear that unevenness develops in a microstructure such as the fiber shape, the pore/surface opening. From this, it is preferred to put a certain upper limit for the modification degree, and the limit is set to 6.6 in embodiments of the present invention, it is preferably 4.5, and more preferably 3.6.

Referring to a method of measuring the modification degree, both ends of fibers which are measurement-object are fixed with tension of 0.1 g/mm² applied to the fibers, and cut at a random position. Thereafter, a cut surface is enlarged with an optical microscope, for example, DIGITAL MICROSCOPE DG-2 manufactured by Scalar Corporation, and photographed. In photographing, a scale is also photographed at the same magnification. After the images are digitized, a diameter of the circumscribed circle Do and a diameter of an inscribed circle Di of the cross section of the fiber are measured using, for example, an image analysis software "Micro Measure ver.1.04" manufactured by Scalar Corporation. Then, the modification degree of each fiber is determined from the following formula. This measurement is carried out at 30 locations, and measured values are averaged and a value obtained by rounding the second place of decimals of the average value is defined as a modification degree.

Modification degree=Do/Di

Further, the porous fibers in embodiments of the present invention have pores inside the fiber. Therefore, a lower limit of an average pore radius of the pore within the porous fiber is preferably 0.5 nm, more preferably 1.5 nm, and particularly preferably 2.0 nm. On the other hand, an upper limit of the average pore radius is preferably 100 nm, more preferably 40 nm, and particularly preferably 25 nm. Even though the inside of the fiber has pores, in the case of a small average pore size, adsorption efficiency may be reduced since the material to be adsorbed does not enter the pore.

On the other hand, when the pore size is too large, adsorption efficiency may be inversely reduced since the material to be adsorbed is not adsorbed on a cavity portion. An optimum pore size is present according to a size of the material to be adsorbed which is a removal-object within the above-mentioned pore size range. Therefore, if a pore size is selected by mistake, sometimes it is impossible to adequately adsorb the material to be adsorbed.

The average pore radius of the porous fibers is determined as a primary average pore radius by measuring a freezing point depression by capillary condensation of water in a pore by differential scanning calorimetry (DSC) using a differential scanning calorimeter (DSC). That is, an adsorbent material is rapidly cooled to −55° C., and a temperature is raised to 5° C. at a rate of 0.3° C./min, and measurement is carried out. A peak-top temperature of the resulting curve is taken as a melting point, and a primary average pore radius of a pore is calculated from the following formula.

$$\text{Primary average pore radius [mm]}=(33.30-0.3181\times \text{melting point depression [° C.]})/\text{melting point depression [° C.]}$$

In addition, in the above measurement/calculation methods, a description in Non-patent Document 1 described above is referred to.

The porous fibers of the present invention can improve the adsorption performance by increasing a pore specific surface area in order to adsorb the material to be adsorbed. Therefore, a lower limit of the pore specific surface area is 50 $m^2/g$, preferably 90 $m^2/g$, more preferably 120 $m^2/g$, still more preferably 170 $m^2/g$, and particularly preferably 250 $m^2/g$. On the other hand, when the pore specific surface area is too large, mechanical strength is insufficient, and therefore an upper limit of the pore specific surface area is preferably 1000 $m^2/g$, more preferably 800 $m^2/g$, still more preferably 650 $m^2/g$, and particularly preferably 500 $m^2/g$.

Measurement of the pore specific surface area is performed with use of DSC as with the measurement method of the average pore radius. A calculation method of the pore specific surface area is as described in Non-patent Document 1.

In the porous fibers according to the present invention, a cross section of the fiber may be a heterogeneous structure or may be a homogeneous structure. Particularly, the fiber having a homogeneous structure is preferred since it has a homogeneous structure in a thickness direction of the fiber and therefore more adsorption area can be secured.

However, the porous fibers may have such a slightly gradient structure that a pore at a periphery of the fiber is enlarged and a pore size is gradually reduced toward a fiber central portion in order to reduce resistance of diffusion to the fiber central portion. Further, in such a condition that pores at the outermost surface of the fiber is completely blocked due to fouling over time, a risk that even pores inside the fiber is blocked is reduced by having such a gradient structure. Consequently, it is possible to suppress a phenomenon in which diffusion of the material to be adsorbed to the fiber central portion deteriorates. In such a homogeneous structure, a ratio of an average pore size in a near-outer surface region of the fiber to an average pore size in a central region of the fiber (average pore size in a near-outer surface region/average pore size in a central region) is 0.50 time or more and 3.00 times or less, more preferably 0.75 time or more and 2.00 times or less, and still more preferably 0.90 time or more and 1.50 times or less. Further, a heterogeneous structure having a macrovoid as often observed for fibers prepared by a nonsolvent induced phase separation method, is not preferred since it reduces a surface area per volume and deteriorates physical properties of the fiber. The macrovoid referred to herein is a spherical pore having a diameter of 25 μm or more. The diameter referred to herein refers to a minor diameter of a pore in the case where a shape of the pore is other than a sphere, for example, an egg shape.

Next, a method of determining a homogeneous structure in the present invention will be described.

First, the porous fibers are adequately moistened, and then immersed in liquid nitrogen to freeze a water content within pores momentarily with liquid nitrogen. Thereafter, the fiber is quickly folded, frozen water content is removed with a fiber cross section exposed in a vacuum drier of 0.1 torr or less to obtain a dry sample. Thereafter, a thin film of platinum (Pt) or platinum-palladium (Pt—Pd) is formed on the surface of the fiber by sputtering to form an observation sample. The cross section of the sample is observed using a scanning electron microscope (e.g., manufactured by Hitachi High-Technologies Corp., S-5500). Here, a radius passing through a center point of a fiber cross section is arbitrarily selected, and concentric circles passing through points which divides a line segment of radius into five equal lengths, as shown in FIG. 2, are drawn, and a region including a center point is referred to as a central region, and a side which is the closest to a periphery is referred to as a near-outer surface region.

A circle equivalent diameter which is present in each of the central region and the near-outer surface region is determined to obtain an average pore size in each region. In calculating the average pore size in each region, using a scanning electron microscope (magnification: 50000 times), areas of 2 μm×2 μm of 20 location are arbitrarily selected and photographed, and a pore whose whole body is included in a photograph taken is measured and an average pore size is calculated. In measurement of a pore size, a transparent sheet is overlaid on a printed electron microscope image, and a pore portion is blacked out using a black marker. Thereafter, by copying the transparent sheet on a white paper, a black pore area is clearly discriminated from a white non-pore area, and a pore size is determined using an image analysis software.

When the ratio of an average pore size in a near-outer surface region of the fiber to an average pore size in a central region of the fiber (average pore size in a near-outer surface region/average pore size in a central region) is 0.50 time or more and 3.00 times or less, it is assumed that the porous fibers have a homogeneous structure. The above-mentioned ratio of average pore size is more preferably 0.75 time or more and 2.00 times or less, and still more preferably 0.90 time or more and 1.50 times or less.

Further, a pore size distribution index of the porous fibers is preferably 1.0 or more and 2.8 or less, and an upper limit thereof is more preferably 2.4, and still more preferably 1.9. The reason for this is that it is possible to impart selectivity of a size of the material to be adsorbed by making a pore size distribution uniform as far as possible. When the pore size distribution index is more than 2.8, it is not preferred since non-specific adsorption is increased.

The pore size distribution index is determined by a measurement method using DSC as with the average pore size, and a value obtained by dividing a secondary average pore radius by a primary average pore radius is taken as a pore size distribution index. With respect to detailed measurement/calculation methods, a description in Non-patent Document 1 is referred to.

Moreover, the porous fibers used for the present invention preferably have a three-dimensional network structure. The three-dimensional network structure referred to herein refers to a structure in which an index of pore shape Dxy is controlled.

Index of pore shape in cross section in fiber axis direction Dxy=(pore size in lengthwise direction of fiber)/(pore size in direction of cross section of fiber)

A lower limit of Dxy is preferably 0.2, more preferably 0.4, and still more preferably 0.6. An upper limit of Dxy is preferably 6.0, more preferably 4.0, and still more preferably 2.5. Since fibers prepared by a stretch-opening method or the like has a characteristic oriented structure in a fiber lengthwise direction, the fibers generally have a structure in which Dxy is very high, it is less-than-preferred.

A method of measuring Dxy is described below. A double-faced tape was bonded to a plate of plastic such as polystyrene and a measurement-object fiber is fixed thereon. The bonded fiber is cut in the lengthwise direction with a one blade to expose a cross section in the lengthwise direction of the fiber, and bonded to a sample stage of a scanning electron microscope with a double-faced tape. Cutting requires caution since exact images cannot be obtained if pores are crushed due to this cutting. Thereafter, a thin film of platinum (Pt) or platinum-palladium (Pt—Pd) is formed on the surface of the fiber by sputtering to form an observation sample. A cross section in the lengthwise direction of the fiber is observed at a magnification of 50000 times using a scanning electron microscope of a field emission type (e.g., manufactured by Hitachi High-Technologies Corp., S-5500), and images of 10 points arbitrarily selected are captured in a computer. A size of images to be captured is preferably 640 pixel×480 pixel. From one image thus obtained, 5 pores are arbitrarily extracted, and a pore size in the lengthwise direction of the fiber, a pore size in the direction of a fiber axis and a ratio between both pore sizes of each pore are determined. This procedure is carried out for the above-mentioned images of 10 points to determine the above ratio for total 50 pores, an average of these ratios is calculated, and a value obtained by rounding the second place of decimals of the average is defined as Dxy.

In order to make the adsorption performance enough, it is important to control a thickness of the dense layer which is present in the vicinity of the surface in the porous fiber. When the thickness of the dense layer is too large, the material to be adsorbed cannot be effectively diffused to the pores within the fibers, resulting in deterioration of the adsorption performance. Therefore, a dense layer thickness in the near-surface region of fibers is preferably 3.90 μm or less, still more preferably 2.10 μm or less, and particularly preferably 1.60 μm or less. Further, when the dense layer is not present, that is, in the case of the fiber in which an internal three-dimensional network structure is exposed to an outside, there is a possibility that the three-dimensional network structure is damaged by application of an external physical force since the three-dimensional network structure is dynamically brittle. As a result of this, there is also a possibility that the adsorption performance is deteriorated or fine particles generated due to damages flow out of the column. Moreover, it is preferred from the viewpoint of stably maintaining the modified cross section shape that a dense layer of 0.01 μm or more is present.

In order to measure the dense layer thickness in the near-surface region of fibers, fiber cross sections which are obtained by the same method as in the observation sample prepared in determination of the homogeneous structure described above, are used. Cross sections of the fibers is observed at a magnification of 30000 times using a scanning electron microscope (e.g., manufactured by Hitachi High-Technologies Corp., S-5500), and images are captured in a computer. A size of images to be captured is preferably 640 pixel×480 pixel. Next, the fiber is observed with SEM to measure a pore size of a pore which can be identified in a fiber cross section. Here, when a pore in the cross section is blocked, preparation of a sample is redone. In addition, blocking of a pore may occur by modification of a fiber due to stress applied during cutting the porous fiber. A SEM image is cut out in the form of a rectangular body having a length of 6 μm in a direction parallel to the surface of the porous fiber and an arbitrary length in a direction perpendicular to the surface of the porous fiber, and the image is subjected to image analysis by an image processing software. The length in a direction perpendicular to the surface may be a length within which the dense layer falls. A threshold level is determined so that a structure portion constituting a fiber is bright luminance and the other portion is dark luminance by binarization processing and an image in which a bright luminance portion is white and a dark luminance portion is black, is obtained. When the structure portion cannot be separated from the other portion since a difference in contrast in the image is small, the image is cut and separated at a part in which a range of contrast is equal, each separated part is subjected to binarization processing, and then combined with each other and returned to one image. Or, image analysis of the image may be carried out by blacking out an area other than the structure portion. A section of from an outermost layer of the cross section to a back layer is photographed in an image, and there may be cases where a pore is doubly observed in a depth direction, and in this case, a pore on a shallow side is measured. When a part of a pore is present out of an image area of measurement-object, the pore is excluded. The number of pixels of a scale bar indicating a known length in the image, and a length per number of pixels of 1 is calculated. The number of pixels of a pore is measured, and a pore area is determined by multiplying the number of pixels of a pore by a square of length per number of pixels of 1. A diameter of a circle corresponding to a pore area is calculated in the following formula, and this is taken as a pore size. When "3.14" is used as a circular constant, if a pore area is 78.5 (nm$^2$), a pore size is 10 nm.

$$\text{Pore size}=(\text{pore area}/\text{circular constant})^{0.5}\times 2$$

The pore having a pore size of 10 nm or more is identified, and a layer where the pore is not present is considered as a dense layer, and the shortest distance of distances from pores having a pore size of 10 nm or more to the fiber surface, is considered as a thickness of the dense layer. That is, of pores having a diameter of 10 nm or more, 5 points found in increasing order in a distance from fiber surface is picked up, and a vertical line is drawn from each point to a plane which is tangent to the fiber surface, and a distance on the vertical line between the fiber surface and the pore having a diameter of 10 nm or more is determined. Similar measurement is carried out for 10 sheets of images, and a value obtained by rounding the third place of decimals of an average value of total 50 measured data is defined as a dense layer thickness in the near-surface region of a fiber.

Further, as a method of controlling the dense layer thickness in the near-surface region of fibers, a structure control of a fiber surface in a dry part in spinning is important. In order to fix (solidify) a structure of a raw spinning solution having flowability to form a fiber shape, sometimes the raw solution is brought into contact with a poor (non) solvent or cooled. The dry part refers to a portion where after the raw spinning solution is discharged from the spinneret, it runs in the air until it contacts the poor solvent or until the raw spinning solution is completely structurally fixed by cooling. When the raw spinning solution is structurally fixed, a near-surface of the raw solution is in a state in which an energy level is high. Therefore, it is thought that a support component such as a polymer is coagulated in contacting a poor solvent or a moisture contained in the air, and thereby a fiber surface is formed. Therefore, a porous structure of the raw spinning solution needs to be determined to some extent before the raw spinning solution contacts the poor solvent, namely, in a dry part. Specifically, it is important to quickly induce phase separation after discharging the raw solution and to adequately grow and enlarge a pore structure before contacting the poor solvent, and to cool the fiber in the dry part to increase viscosity of the raw solution and thereby to suppress coagulation due to a reduction of mobility of a support component. In order to realize this, it is important to take an adequate retention time in the dry part. Accordingly, the retention time is 0.05 second or more, preferably 0.20 second or more, and more preferably 0.40 second or more. The retention time is calculated by following formula.

Retention time (sec)=dry part length (m)/taken-up speed (m/sec)

The pore area of the fiber surface can be increased by reducing a surface dense layer thickness; A surface pore ratio of the porous fiber is preferably 0.5% or more, more preferably 1.5% or more, and particularly preferably 2.0% or more. When the pore ratio is high, it is preferred since the material to be adsorbed in the fluid that is to be treated is easily diffused to an adsorbing site within the fiber. On the other hand, an upper limit of the surface pore ratio is 30%, still more preferably 16%, and particularly preferably 12%. When the pore ratio is too high, it is not preferred since this results in a reduction of fiber strength or an increase of surface roughness. Further, fine particles produced within a pore easily flow out of the fiber.

As a method of measuring the surface pore ratio, the fiber surface which are obtained by the same method as in the observation sample prepared in determination of the homogeneous structure described above, are observed at a magnification of 50000 times using a scanning electron microscope (manufactured by Hitachi High-Technologies Corp., S-5500), and observed images are captured in a computer. A size of images to be captured is preferably 640 pixel×480 pixel. An area of 6 μm×6 μm of SEM image is cut out at arbitrarily position and subjected to image analysis by an image processing software. A threshold level is determined so that a structure portion is bright luminance and the other portion is dark luminance by binarization processing and an image in which a bright luminance portion is white and a dark luminance portion is black, is obtained. When the structure portion cannot be separated from the other portion since a difference in contrast in the image is small, the image is cut and separated at a part in which a range of contrast is equal, each separated part is subjected to binarization processing, and then combined with each other and returned to one image. Or, image analysis of the image may be carried out by blacking out an area other than the structure portion. A dark luminance portion in which noises are included in the image and number of continuous pixels is five or less is handled as a bright luminance portion as a structure since the noise cannot be discriminated from the pore. A method of eliminating noises includes a method of excluding the dark luminance portion in which number of continuous pixels is five or less in counting the number of pixels. Or, noise portion may be whited out. The number of pixels in the dark luminance portion is counted, and a percentage with respect to the total number of pixels in analysis image is calculated and the percentage is defined as a pore ratio. The same measurement is carried out for 30 images, and an average is calculated.

A shape of the projected part in the porous fiber is important. Examples of an item representing the shape of the projected part include a width of the projected part ω and a projected part form exponent ω/Di.

A definition of the projected part width ω is shown in FIG. 3. A point is determined which divides, into two equal lengths, a line segment (line segment 1) connecting between a point of a tip portion of a projected part and a point at which a straight line connecting between a center of an inscribed circle and a tip portion of a projected part and the inscribed circle intersect, a line passing through the determined point and orthogonally intersecting with the line segment 1 is drawn to both widths of the projected part to make a line segment 2 and a length of the line segment 2 is determined. In specific measurement, as described above, the projected part width is calculated using an optical microscope and an image analysis software, and all projected parts in the fiber cross section were measured and averaged. This work is carried out at 25 locations arbitrarily selected in the fiber cross section, and a value obtained by rounding the third place of decimals of an average value is defined as a projected part width ω.

Di is, as described above, a diameter of an inscribed circle of the fiber cross section measured in determining the modification degree. When ω is too thick, or when ω/D is too large even though the ω is not thick, the fibers come to enter the coagulating bath including a poor solvent with cooling of the projected part in the dry part insufficient. In this case, the support component present in the vicinity of the surface is easily coagulated/deposited, and this may lead to an increase of the dense layer thickness in near-surface region or a reduction of the surface pore ratio. The increase of the dense layer thickness or the reduction of the surface pore ratio tends to interfere with diffusion of the material to be adsorbed to the inside of the pore to cause a significant reduction of the adsorption performance. Therefore, an upper limit of the width of the projected part ω is preferably 200 μm, still more preferably 135 μm, and particularly preferably 100 μm. Further, an upper limit of the ω/Di is preferably 2.0, more preferably 1.6, and still more preferably 1.1. On the other hand, when the ω is too thin or the ω/Di is too small, it is not preferred since bending or chips of the projected part are easily generated and the surface per volume cannot be adequately large. Therefore, a lower limit of the width ω of the projected part is preferably 5 μm, more preferably 10 μm, and still more preferably 25 μm. Further, a lower limit of the ω/Di is preferably 0.05, more preferably 0.10, and still more preferably 0.20.

An upper limit of a circle equivalent diameter of a cross section including the projected part of the porous fiber is preferably 300 μm, more preferably 240 μm, still more preferably 190 μm, and particularly preferably 160 μm. When the circle equivalent diameter is too large, it is not preferred since a packed amount of the fibers per unit volume in packing the fibers in a column is reduced, resulting in a reduction of the surface area per volume.

Further, sometimes fibers enter coagulating bath including a poor solvent without being adequately cooled since cooling efficiency of discharged fibers is lowered or it is difficult to maintain a shape of a fiber resulting in a reduction of the modification degree. In this case, a near-surface support material such as a polymer is easily coagulated/deposited, resulting in an increase of the dense layer thickness in near-surface region or a reduction of the surface pore ratio. On the other hand, a lower limit of the circle equivalent diameter is preferably 10 μm, more preferably 30 μm, and particularly preferably 50 μm. When the circle equivalent diameter is too small, it is not preferred since strength of the fibers is lowered, and stability/productivity of spinning and fibers become brittle. Further, it is conceivable that an adsorption site is easily saturated since a volume per surface area is too small.

Referring to a method of measuring the above-mentioned circle equivalent diameter of a cross section, both ends of fibers which are measurement-object are fixed with tension of 0.01 to 0.1 g/mm² applied to the fibers, and cut. Thereafter, a cut surface is enlarged with an optical microscope, and photographed. In doing so, a scale is also photographed at the same magnification. After the images are digitized, using, for example, an image analysis software "Micro Measure ver.1.04" manufactured by Scalar Corporation, a periphery of the cross section of the fiber is traced to determine a cross-sectional area S, and a circle equivalent diameter of each opening is calculated from the following formula. An average of measurements of 30 points is calculated, and the first place of decimals of the average is rounded.

$$\text{Circle equivalent diameter of cross section} = 2 \times (S/\pi)^{1/2}$$

A material of the porous fibers in the present invention is not particularly limited, however, organic substances are suitably used from the viewpoint of ease of forming process and cost, and polymethylmethacrylate (hereinafter, referred to as PMMA), polyacrylonitrile (hereinafter, referred to as PAN), polysulfone, polyethersulfone, polyarylethersulfone, polypropylene, polystyrene, polycarbonate, cellulose, cellulose triacetate, ethylene-vinyl alcohol copolymer or the like is used. Particularly, the porous fibers preferably contains a material which is hydrophobic to some extent and has a characteristic capable of adsorbing protein, and examples of the material include PMMA, PAN and the like. PMMA and PAN are preferred since they are typical examples of a fiber having a uniform structure in a thickness direction and easily attain a homogeneous structure and a structure in which a pore size distribution is sharp. Further, a polymer containing an ester group is preferred since it has excellent biocompatibility and easily exerts a function by controlling a terminal group. Particularly, PMMA is preferred since it is an amorphous polymer and excellent in forming processability and cost, and has high transparency and therefore observation of an internal state of the fiber is relatively easy to facilitate evaluation of a fouling condition. Further, the porous fibers may have a negative charge. It is also reported that by containing a functional group having a negative charge in at least a part of the material, a hydrophilic property is increased and the material tends to be finely dispersed (that is, many fine pores are formed). Examples of the functional group having a negative charge include a sulfo group, a carboxyl group, a phosphate group, a phosphorous acid group, an ester group, a sulfite group, a hydrosulfite group, a sulfide group, a phenolic group, a hydroxysilyl group and the like. Among these compounds, at least one selected from a sulfo group, a carboxyl group, and an ester group. Examples of compounds having a sulfo group include vinylsulfonic acid, acryl sulfonic acid, methacrylsulfonic acid-p-styrenesulfonic acid, 3-methacryloxypropanesulfonic acid, 3-acryloxypropanesulfonic acid, 2-acrylamide-2-methylpropanesulfonic acid, and sodium salt, potassium salt, ammonium salt, pyridine salt, quinoline salt, tetramethylammonium salt thereof. An amount of a negative charge is preferably 5μ eq or more and 30μ eq or less per 1 g of dried fibers. The amount of a negative charge can be measured using, for example, a titration method.

In production of the porous fibers according to the present invention, viscosity of a raw spinning solution is important for preparation of the porous fibers. That is, the viscosity of the raw spinning solution is too low, flowability of the raw solution is high and therefore it is difficult to maintain a desired shape. Therefore, a lower limit of viscosity of the raw solution is preferably 10 poise, more preferably 90 poise, still more preferably 400 poise, and particularly preferably 800 poise. On the other hand, when the viscosity is too high, stability of discharge is deteriorated or mixing of the raw solution becomes difficult due to an increase of pressure loss at the time of discharging the raw solution. Therefore, an upper limit of viscosity of the raw solution at a temperature of the spinning spinneret part is 100000 poise, and more preferably 50000 poise.

Viscosity measurement is performed by a falling ball method in a thermostatic chamber set to a spinning temperature according to JIS Z 8803. Specifically, a viscosity tube with an inner diameter of 40 mm is filled with a raw spinning solution, and a steel ball (material: SUS 316) of 2 mm in diameter is dropped in the raw solution, and the time required for the ball to fall by 200 mm is measured to determine viscosity. A temperature at the time of measuring is set to 92° C.

In order to prepare the porous fibers according to the present invention, it is important to control the configuration of the discharge opening of the spinning spinneret besides composition of a raw spinning solution and the contrivance at the dry part. Particularly, the porous fibers in the present invention has a very high modification degree. Therefore, in the spinneret which has a shape almost similar to a cross section of a fiber to be obtained as observed for a conventional spinneret design concept, since the cross section area of a discharge opening of the spinneret is large, a draft at the dry part is increased, and an uneven fiber diameter or an uneven modification degree referred to as draw resonance are easily generated, and spinning is difficult. That is, as shown in FIG. 4 and FIG. 5, the configuration of the discharge opening of the spinning spinneret preferably has a central circle portion, a slit portion and a tip circle portion. Further, it is necessary to appropriately design a diameter of the central circle D, a width of the slit portion W, a length of the slit portion L and a diameter of the tip circle d.

The slit portion is important in determining the modification degree, and the modification degree can be improved by increasing a value L/W obtained by dividing the length of the slit portion L by W. Therefore, a lower limit of the L/W is preferably 1.9, more preferably 2.8, still more preferably 5.5, and particularly preferably 9.5. On the other hand, when the L/W is too large, the shape of the projected part of the fiber is narrow and unstable, and the agglutination of the projected part easily occurs within a single yarn. Therefore, an upper limit of the L/W is 50, and particularly preferably 20.

The tip circle diameter d preferably has a value of a certain value or more in forming a shape of a modified cross section, and the projected part width can be controlled by changing d. That is, the projected part width and the projected part form exponent ω/Di can be increased as d is increased. However, too large projected part width and ω/Di cause the enlargement of the tip portion to cause modification of a cross-section shape (agglutination of the projected part within a single fiber) due to insufficient cooling in the dry part, an increase of a dense layer thickness in the surface in the enlarged portion, and a reduction of the surface pore ratio. Therefore, an upper limit of the d is 1.0 mm, more preferably 0.6 mm, and particularly preferably 0.3 mm.

When a value of W is too small, the pressure loss at a spinneret portion is increased, influence of the Barus effect becomes large, or processing of the spinneret itself becomes difficult. Therefore, a lower limit of the W is 0.005 mm, more preferably 0.010 mm, and still more preferably 0.030 mm. On the other hand, when the W is too large, a cross section area of a discharge part is increased, a draft at the dry part is increased, and an uneven fiber diameter or an uneven modification degree referred to as draw resonance are easily generated, and spinning is difficult. An upper limit of the W is 1.00 mm, more preferably 0.50 mm, and still more preferably 0.25 mm.

The central circle 9 does not have to exist; however, it preferably exists for controlling the cross-section shape of the fiber with a modified cross section. That is, a flow rate of a central portion can be increased in the entire spinneret by providing the central circle 9. Therefore, the projected part width and the projected part form exponent ω/Di can be decreased as D is increased.

Further, when a wind velocity of cool air of the dry part is too high, modification of a cross-section shape, particularly, agglutination in a single yarn between the projected parts in a single fiber cross section, may occur. On the other hand, when the wind velocity is too low, fixation of the fiber shape becomes difficult resulting in the variations of a yarn diameter and a fiber shape. Therefore, a lower limit of a cool air velocity is preferably 0.5 m/s, more preferably 0.8 m/s, and still more preferably 1.5 m/s. An upper limit is preferably 20.0 m/s, more preferably 15.0 m/s, and still more preferably 11.0 m/s.

An application of the porous fibers in the present invention is of great variety, and the porous fibers can be used in various fields such as medical care, water treatment and purification. Particularly, in a medical care application, the porous fibers are suitably used for removal of pathogenic proteins, bacteria and virus from blood and blood plasma, or a body fluid. Examples of pathogenic proteins include cytokine, β$_2$-microglobulin (β$_2$-MG), IgG, immune complexes, LDL and the like. In addition to this, when used in water treatment, the porous fibers are suitably used for removal of humic substances, metal corrosion products and the like.

As a spinning method for obtaining the fibers in the present invention, any of melt spinning and solution spinning can be employed; however, the solution spinning is preferred since in the solution spinning, a porous fiber having a relatively uniform structure is easily attained by quickly removing only a solvent from a state in which a support component is uniformly dissolved in the solvent. Therefore, the raw spinning solution preferably includes a support component such as a resin and a good solvent in which the support component can be dissolved. Although a third component such as fine particles can be mixed as a pore-forming material or a dispersant, there is a possibility that washing efficiency may be deteriorated or fixation by post-crosslinking may be required depending on use conditions.

When the adsorption performance per volume of porous fibers is low, the porous fibers are not preferred as an adsorbent material and do not exhibit good adsorption performance even though being packed in a column or the like. In order to ensure the adsorption performance, the number of fibers to be packed is forced to be increased, and this leads to an increase of a column volume to cause a cost rise and a reduction of handleability. Particularly, when the fluid that is to be treated is blood, since an amount of blood to be brought out of the body is increased, there is a possibility that a serious side effect such as a blood pressure drop is developed. Thus, when the material to be adsorbed is the β$_2$-MG, the adsorption performance per volume of fibers is preferably 0.005 mg/cm$^3$ or more, more preferably 0.014 mg/cm$^3$ or more, still more preferably 0.020 mg/cm$^3$ or more, and particularly preferably 0.031 mg/cm$^3$ or more.

The adsorption performance of the fibers can be easily measured by a batch process by using β$_2$-MG, as an adsorption object, which is a pathogenic protein of dialysis-related amyloidosis of complicating disease of long-term dialysis.

A method of measuring the adsorption performance is as follows. First, cattle blood to which disodium ethylenediamine tetraacetate is added is adjusted so that an amount of total protein is 6.5±0.5 g/dL. In addition, a bovine blood plasma within 5 days after blood draw is used. Next, β$_2$-MG is added so as to have a concentration of 1 mg/L and the resulting mixture is stirred.

Moreover, the porous fibers were cut into a bundle of 8 cm in length, and the bundle was put in, for example, a 15 mL centrifuge tube manufactured by GREINER Japan Co., so that a volume of the fibers is 0.0905 cm$^3$, and to this, 12 mL of the above bovine blood plasma was added, and the resulting mixture was stirred at room temperature (20° C. to 25° C.) for 1 hour using a seesaw shaker, for example, Wave-SI manufactured by TAITEC CORPORATION and setting a scale to 38 and an angle to maximum (one turn in 1.7 seconds). In order to measure the β$_2$-MG concentration before stirring C1 (mg/mL) and the β$_2$-MG concentration after stirring C2 (mg/mL), 1 mL of a sample was taken before and after stirring and stored in a freezer of −20° C. or lower. The β$_2$-MG concentration was measured by latex agglutination, and an adsorbed amount per fiber volume and an adsorbed amount per fiber surface area are calculated from the following expressions.

Adsorbed amount per fiber volume (mg/cm$^3$)=(C1−C2)×12/0.0905

Adsorbed amount per fiber surface area (μg/cm$^2$)= (C1−C2)×12/(total surface area of fibers cm$^2$)× 1000

The porous fibers in the present invention can be used as a purification column by being incorporated into a casing having an inlet and an outlet of the fluid that is to be treated.

Examples of a shape of the casing include angular tubular bodies such as a square tubular body and a hexagonal tubular body, and a cylindrical body, in which both ends are an open end, and among these, the cylindrical body, particularly, a tubular body with a completely circular cross section is preferred. The reason for this is that since the casing does not have a corner, stagnation of blood at a corner portion can be suppressed. Further, since both sides are each an open end, a flow of the fluid that is to be treated hardly becomes turbulent and therefore a pressure loss can be minimized. Further, the casing is preferably an instrument composed of plastic, metal or the like. When the plastic is used, for example, a thermoplastic resin having excellent mechanical strength and excellent heat stability is used. Specific examples of such a thermoplastic resin include polycarbonate-based resins, polyvinyl alcohol-based resins, cellulose-based resins, polyester-based resins, polyarylate-based resins, polyimide-based resins, cyclicpolyolefin-based resins, polysulfone-based resins, polyethersulfone-based resins, polyolefin-based resins, a polystyrene resin, polyvinyl alcohol-based resins, and mixtures thereof. Among these resins, polypropylene, polystyrene, polycarbonate and derivatives thereof are preferred from the viewpoint of formability and radiation resistance. Particularly, resins having excellent transparency such as polystyrene and polycarbonate are favorable for ensuring safety since an internal state can be recognized in perfusing blood or the like. Resins having excellent radiation resistance are preferred in the case where radiation is performed at the time of sterilization. The resin is manufactured by injection molding by a die or machining of a material. Particularly, plastic is suitably used from the viewpoint of cost, formability, weight and adaptability to blood.

As a method of sealing an end of the purification column, there are a method of disposing a mesh, and a method in which the end is fixed using a rein, a penetrating hole penetrating through a partition wall is provided and thereby inside of the casing is communicated with outside. Here, the penetrating hole is an opening which penetrates through a partition wall part in the lengthwise direction of the porous fiber. That is, the penetrating hole is present in the partition wall part and penetrates through the partition wall part, and refers to a pore through which inside of the casing is communicated with outside. Among these method, the method of disposing a mesh is more preferred than the method of forming a partition wall since a process is easier and dispersibility of liquid in the column is higher. Further, a mesh having a larger pressure loss or a plate which blocks a flow and is referred to as a baffle may be provided for a part of the mesh for the purpose of further enhancing the dispersibility of the fluid that is to be treated in a column.

When a casing length of the purification column is excessively long, it is thought that insertion of the porous fibers into a column is deteriorated or handling in actually using as a purification column becomes difficult. Further, when the casing length is excessively short, it becomes disadvantageous, for example, in the case of forming a partition wall part or handleability in forming the fibers into a column is low. Therefore, the casing length of the purification column is 1 cm or more and 500 cm or less, and still more preferably 3 cm or more and 50 cm or less. Herein, the casing length is a length in an axis direction of a tubular casing before partition walls are disposed or caps are fitted.

As a shape of the fibers in incorporating into a column, a straight form is preferred, and it is preferred to insert the fibers of the straight form in parallel to a lengthwise direction of a column case. Since the porous fibers of the straight form easily secure a flow path of the fluid that is to be treated, it is easy to uniformly distribute the fluid that is to be treated in the column. Further, such fibers can suppress resistance of the flow path, and is advantageous to an increase of a pressure loss due to the adhesion of a dissolved substance in the fluid that is to be treated. Therefore, even when highly viscous blood is a fluid that is to be treated, a risk of coagulation in the casing can be kept low. The porous fibers can also be processed as a knit, a fabric or a nonwoven fabric or cut into grains of less than 5 mm. However, since large tension or stress is applied to the fiber in processing or shredding, there is such a restriction that a pore ratio of the fiber cannot be increased. Moreover, the number of process steps increases by processing the fibers, and cost also increases. Further, when the fluid that is to be treated includes many dissolved substances and viscosity is high, it is not so preferred since processing easily results in a pressure rise in a column.

The number of fibers of the straight form to be inserted into the column is preferably 1000 to about 500000.

In the present invention, it is an object to provide porous fibers in which the material to be adsorbed enters the inside of the fibers and is adsorbed. Thus, it is preferred that fibers have such a form and a structure that the material to be adsorbed easily moves to the inside of the fiber. Furthermore, in the present invention, it is found that the material to be adsorbed easily moves to the inside of the porous fiber when a pressure loss is large. However, too large pressure loss affects a dissolved substance, other than the material to be adsorbed. From this viewpoint, a suitable range is present for the pressure loss of the column, and it is preferred that the pressure loss at the time of passing a bovine blood plasma through a column at a flow rate of 200 mL/min, is 0.5 kPa or more and 30 kPa or less. A lower limit of the pressure loss is more preferably 0.7 kPa, and still more preferably 1 kPa. An upper limit of the pressure loss is more preferably 21 kPa, and still more preferably 9 kPa. The pressure loss can be controlled by the packing ratio of the fibers in a column, the casing inner diameter, the fiber diameter and the number of fibers. In the present invention, an upper limit of the packing ratio of the fibers to a casing is preferably 70%, more preferably 65%, and particularly preferably 62%. A lower limit of the packing ratio is preferably 30%, more preferably 45%, and particularly preferably 52%. Too high packing ratio causes poor insertion of fibers into a case, and too low packing ratio leads to deviation of fibers in a case to cause uneven flow in a column.

The packing ratio is a ratio between a casing volume (Vc) which is calculated from a cross section area and a length of a casing and a fiber volume (Vf) calculated from a fiber cross section area of a fiber, a casing length and the number of fibers, and determined as follows.

Vc=Cross section area of casing body×appropriate length

Vf=Cross section area of a fiber×number of fibers× appropriate length

Vf/Vc×100(%)

When the casing has a tapered portion, the cross section area of the casing body is a cross section area at a middle section of the casing.

The Vc referred to herein does not include a volume of a member not containing fibers which serves as outlet/inlet ports of the fluid that is to be treated, such as members referred to as a header or a header cap. Further, the Vf also includes a volume of spacer fibers or the like in the case where the spacer fibers for preventing intimate contact between fibers in a case or the like are used. The appropriate length of fiber refers to a length obtained by subtracting a length of partition walls from the casing length, and an upper limit of the appropriate length of a fiber is preferably 5000 mm, more preferably 500 mm, and particularly preferably 210 mm from the viewpoint that the pressure loss increases when fibers are bent or incorporated in a column. Further, when the appropriate length is too short, it is not preferred since an amount of fibers to be disposed in cutting extra fibers protruding out of a column in order to align lengths of fibers, is increased resulting in a reduction of productivity. Further, there is a disadvantage that handling of the fiber bundle becomes difficult. Therefore, a lower limit of the appropriate length of a fiber is preferably 5 mm, more preferably 20 mm, and particularly preferably 30 mm. In measurement of the appropriate length of a fiber, a fiber length is measured in a state of straight form in which both ends of the fiber are stretched in the case of a crimped fiber. Specifically, one side of fiber taken out of the column is fixed with a tape or the like and hung vertically, and to the other side, a weight of about 8 g per cross section area ($mm^2$) of the fiber is provided and a whole length is quickly measured when the fiber becomes straight. This measurement is carried out on 30 fibers arbitrarily selected in a column or the like, an average of 30 fibers is calculated in millimeters, and the first place of decimals of the average is rounded.

Further, when the fibers are used as a fiber bundle, it is preferred to include many porous fibers in the present invention in the bundle from the viewpoint of enhancing a specific surface area per volume of the fiber, and it is possible to combine with fibers having a cross section with another shape such as a fiber with a circular cross section or an elliptic fiber in which the number of projected parts is two. A ratio of the porous fibers of embodiments of the present invention in the fiber bundle is 18% or more, more preferably 33% or more, still more preferably 67% or more, and particularly preferably 90% or more. The fiber bundle thus obtained can be suitably used as an adsorbent material having high adsorption performance.

Applications of such a fiber bundle and a purification column into which the fiber bundle is incorporated are of great variety, and these can be used for applications such as water treatment, purification and medical care. Among these applications, in the case of a medical care application, a treatment method includes a method of directly perfusing total blood, and a method in which the blood plasma or blood serum is separated from the blood and then the blood plasma or the blood serum is passed through a column, and the purification column of the present invention can be used for both methods.

Further, when the purification column is used as a medical equipment, a technique in which the column is incorporated into an extracorporeal circulation circuit and adsorption/removal are performed online, is preferred from the viewpoint of an amount of one throughput or ease of operation. In this case, the purification column of the present invention may be used singly, or may be connected to an artificial kidney in series at the time of dialysis for use. By using such techniques, it is possible to remove a substance, concurrently with dialysis, which is inadequately removed only by the artificial kidney. Particularly, a function of the artificial kidney can be complemented by adsorbing/removing a substance having a large molecular weight which is hard to be removed by the artificial kidney, using the purification column according to the present invention.

When the purification column is used concurrently with the artificial kidney, it may be connected prior to the artificial kidney or post to the artificial kidney in a circuit. An advantage of connecting prior to the artificial kidney is that the purification column easily exerts its inherent performance since it is hardly affected by the dialysis by the artificial kidney. On the other hand, an advantage of connecting post to the artificial kidney is that a concentration of a dissolved material is high since blood after water is removed in the artificial kidney is processed, and an increase of adsorption/removal efficiency can be expected.

Preparation examples of the porous fibers according to the present invention and the purification column into which the porous fibers are incorporated will be described below.

[Preparation of Porous Fibers]

A raw spinning solution which is formed by dissolving a polymer in a solvent is adjusted. In this time, since the lower the concentration (concentration of a substance in the raw solution excluding a solvent) of the raw solution is, the larger a pore size of a fiber can be, it is possible to control a pore size/a pore amount by appropriately setting the raw solution concentration. In addition to this, it is also possible to control a pore size/a pore amount by using a polymer having a negatively charged group. From such a viewpoint, in the present invention, the raw solution concentration is preferably 30 wt % or less, more preferably 27 wt % or less, and still more preferably 24 wt % or less. Further, when the polymer having, for example, methacrylsulfonic acid-p-styrenesulfonic acid as a negatively charged group, is used, a ratio of the polymer having methacrylsulfonic acid-p-styrenesulfonic acid which is present in the total polymers, is preferably 10 mol % or less. The fiber is obtained by using a spinneret having, for example, a discharge opening with a modified cross section as shown in FIG. 5 (D=0.20 mm, W=0.10 mm, L=1.0 mm, d=0.25 mm), passing the raw solution through the dry air portion having a certain distance, and then discharging the raw solution in a coagulating bath including a poor solvent such as water, or a nonsolvent. From the above-mentioned viewpoint, a lower limit of a transit (retention) time of fibers in the dry part is as described above. Further, when a temperature of the discharged fiber is lowered in a dry part and the fiber is gelated or coagulated and rapidly structurally fixed, gelation of the fiber can be promoted by blowing a cool air on the fiber in the dry part. Further, although a detailed mechanism is not clear, by increasing a cool air velocity to increase cooling efficiency, it is possible to increase the pore ratio of the fiber surface and a pore size in the near-periphery of the fiber. The raw spinning solution discharged from the spinneret is coagulated in a coagulating bath. The coagulating bath generally includes a mixture of a coagulating agent such as water or alcohol, or a solvent constituting the raw spinning solution. Usually, water is used. Further, the pore size can be varied by controlling a temperature of the coagulating bath. Since the pore size can be affected by the type of the raw spinning solution, a temperature of the coagulating bath is also appropriately selected. In general, when coagulating bath temperature is elevated, the pore size can be enlarged. The mechanism is not precisely clear, it is conceivable that the raw solution may be coagulated/fixed before the inside of the fiber contracts since removal of the solvent is fast in a high-temperature bath by a competition reaction of removal of the solvent from the raw solution and coagulation/contraction the raw solution. However, when the coagulating bath temperature is too high, the pore size is excessively large, and therefore, it is thought that the specific surface area and strength-elongation are reduced, and nonspecific adsorption increases. Therefore, for example, a temperature of coagulating bath in the case where the fiber contains PMMA is preferably 90° C. or lower, more preferably 75° C. or lower, and particularly preferably 65° C. or lower. On the other hand, when the temperature of coagulating bath is too low, a pore diameter is reduced and the material to be adsorbed is hardly diffused to the inside of the pore. Therefore, a lower limit of the temperature of coagulating bath is preferably 12° C., and more preferably 20° C.

Then, the fibers are washed in order to remove a solvent adhering to the coagulated fibers. A means for washing the fibers is not particularly limited, and a method of passing the fibers through a multi-stage bath filled with water (referred to as a water washing bath), is preferably used. A temperature of water in the water washing bath may be determined according to properties of a polymer constituting the fiber. For example, in the case of a fiber containing PMMA, a temperature of 30° C. to 50° C. is employed.

Further, a process step of providing a moisturizing ingredient for the fibers to maintain a pore size of the pores after water washing bath, may be added. The moisturizing ingredient referred to herein refers to an ingredient capable of retaining a humidity of the fibers, or an ingredient capable of preventing a reduction of a humidity of the fibers in the air. Typical examples of the moisturizing ingredient include glycerin and an aqueous solution thereof.

After the completion of water-washing and providing of a moisturizing ingredient, in order to enhance the dimension stability of the highly contractive fiber, the fibers can be passed through a bath filled with a heated aqueous solution of the moisturizing ingredient (heat treatment bath). The heat treatment bath is filled with a heated aqueous solution of the moisturizing ingredient, and if the fibers are passed through the heat treatment bath, the fibers undergo thermal actions to contract, and hardly contract in the subsequent steps, and thereby the fiber structure can be stabilized. A heat treatment temperature in this case, varying according to a material, is preferably 50° C. or higher and more preferably 80° C. or higher in the case of a fiber containing PMMA. Further, the heat treatment temperature which is preferably 95° C. or lower and more preferably 87° C. or lower is set.

[Preparation of Purification Column]

An example of a means for forming a purification column using the resulting fibers, is as follows. First, a plurality of fibers is cut to a required length, a required number of fibers are bundled, and the resulting fiber bundle is put in a plastic casing serving as a tube part of the purification column in the straight form in a direction of a case axis. The number of fibers to be bundled is determined according to the application of the purification column, and it is preferably about 5000 to 20000. Thereafter, both ends of the fibers are cut with a cutter so that the fibers are housed in the casing, and mesh filters which are cut to a size having a diameter equal to a casing inner diameter are fitted to the inlet/outlet of the fluid that is to be treated at both column end surfaces at both ends of the column. Finally, an inlet port and an outlet port of the fluid that is to be treated which are referred to as a header cap, are attached to both ends of the casing, and thereby a purification column can be obtained.

Further, when the purification column is used as a medical device or the like, that is, as an adsorption column for medical use, the column is preferably used antiseptically or under sterilization. As a method of disinfection or sterilization, various methods of disinfection or sterilization, such as high-pressure steam sterilization, gamma sterilization, electron beam sterilization, ethylene oxide gas sterilization, drug disinfection, and ultraviolet ray disinfection can be exemplified. Among these methods, gamma sterilization, electron beam sterilization, high-pressure steam sterilization, and ethylene oxide gas sterilization are preferred from the viewpoint of sterilization efficiency and less effect on a material.

EXAMPLES

Example 1

[Preparation of Porous Fibers]

Syn-PMMA (31.7 parts by mass) having a mass average molecular weight of 400000, syn-PMMA (31.7 parts by mass) having a mass average molecular weight of 1400000, iso-PMMA (16.7 parts by mass) having a mass average molecular weight of 500000, and PMMA copolymer (20 parts by mass) having a molecular weight of 300000 containing 1.5 mol % of sodium p-styrenesulfonate were mixed with dimethyl sulfoxide (376 parts by mass), and the resulting mixture was stirred at 110° C. for 8 hours to prepare a raw spinning solution. Viscosity at 92° C. of the prepared raw spinning solution was 1880 poise. The raw spinning solution was discharged at a rate of 1.1 g/min from a spinneret maintained at 92° C. and having a discharge opening which had a configuration shown in FIG. 5 and dimensions shown in Table 1 into the air. The discharged raw spinning solution run 380 mm through the air portion, was guided to a coagulating bath and passed through the bath to obtain solid-state fibers. Water was used for the coagulating bath and a water temperature (coagulating bath temperature) was 42° C. Each fiber was washed with water, guided to a bath tank including an aqueous solution containing glycerin in an amount of 70 wt % as a moisturizing agent, and passed through a heat treatment bath at 84° C. to remove extra glycerin and wound at a rate of 16 m/min.

With respect to the obtained fibers, measurement of the modification degree/projected part width of a fiber cross section, the projected part form exponent, the circle equivalent diameter, the average pore radius, the pore size distribution index and the surface pore ratio, measurement of the dense layer thickness in the near-surface region, and measurement of the adsorption performance per surface area/per volume were performed with use of the above-mentioned techniques. The results are shown in Table 2.

Example 2

Fibers were prepared under the same conditions as in Example 1 except for using a spinneret having a configuration shown in FIG. 5 and having a discharge opening with dimensions shown in Table 1. The results are shown in Tables 1 and 2.

Example 3

Fibers were prepared under the same conditions as in Example 1 except for using a spinneret having a configuration shown in FIG. 5 and having a discharge opening with dimensions shown in Table 1. The results are shown in Tables 1 and 2.

Example 4

Fibers were prepared under the same conditions as in Example 1 except for using a spinneret having a configuration shown in FIG. 5 and having a discharge opening with dimensions shown in Table 1. The results are shown in Tables 1 and 2.

Example 5

Fibers were prepared under the same conditions as in Example 1 except for using a spinneret having a configuration shown in FIG. 5 and having a discharge opening with dimensions shown in Table 1. The results are shown in Tables 1 and 2.

Example 6

Fibers were prepared under the same conditions as in Example 1 except for using a spinneret having a configuration shown in FIG. 5 and having a discharge opening with dimensions shown in Table 1. The results are shown in Tables 1 and 2.

Comparative Example 1

Fibers were prepared under the same conditions as in Example 1 except for using a spinneret having a configuration shown in FIG. 5 and having a discharge opening with dimensions shown in Table 1. The results are shown in Tables 1 and 2.

Comparative Example 2

Fibers were prepared under the same conditions as in Example 1 except for using a spinneret having a configuration shown in FIG. 5 and having a discharge opening with dimensions shown in Table 1. The results are shown in Tables 1 and 2.

Comparative Example 3

Fibers having a circular cross section were prepared under the same conditions as in Example 1 except for using a spinneret having a circular discharge opening of 0.3 in diameter φ. The results are shown in Tables 1 and 2.

Comparative Example 4

Fibers were prepared under the same conditions as in Example 1 except for using a spinneret having a configuration shown in FIG. 9 and having a discharge opening with dimensions shown in Table 1. The results are shown in Tables 1 and 2.

TABLE 1

| | Configuration/Dimension of Spinneret | | | | | | | | |
|---|---|---|---|---|---|---|---|---|---|
| | Spinneret Configuration (Drawing No.) | D (mm) | W (mm) | L (mm) | L/W | d (mm) | Discharge Amount cc/min | Transit Time in Dry Part sec | Cool Air Velocity m/s |
| Example 1 | FIG. 5 | 0.20 | 0.10 | 0.5 | 5.0 | 0.25 | 1.1 | 1.42 | 2.5 |
| Example 2 | FIG. 5 | 0.20 | 0.10 | 0.7 | 7.0 | 0.25 | 1.1 | 1.42 | 2.5 |
| Example 3 | FIG. 5 | 0.20 | 0.10 | 1.0 | 10.0 | 0.25 | 1.1 | 1.42 | 2.5 |
| Example 4 | FIG. 5 | 0.20 | 0.10 | 1.5 | 15.0 | 0.25 | 1.1 | 1.42 | 2.5 |
| Example 5 | FIG. 5 | 0.20 | 0.10 | 2.0 | 20.0 | 0.25 | 1.1 | 1.42 | 2.5 |
| Example 6 | FIG. 5 | 0.20 | 0.10 | 2.5 | 25.0 | 0.25 | 1.1 | 1.42 | 2.5 |
| Comparative Example 1 | FIG. 5 | 0.20 | 0.10 | 3.5 | 35.0 | 0.25 | 1.1 | 1.42 | 2.5 |
| Comparative Example 2 | FIG. 5 | 0.25 | 0.10 | 1.0 | 10.0 | 0.10 | 1.1 | 1.42 | 2.5 |
| Comparative Example 3 | circle of 0.3 in diameter φ | — | — | — | — | — | 1.1 | 1.42 | 2.5 |
| Comparative Example 4 | FIG. 9 | — | 0.30 | 0.8 | 2.7 | — | 1.1 | 1.42 | 2.5 |

| | Temperature of Coagulating Bath °C. | Taken-up Speed m/min | Number of Projected Parts | Modification Degree Do/Di | Projected Part Width ω μm | Projected Part Form Exponent ω/Di |
|---|---|---|---|---|---|---|
| Example 1 | 43 | 16 | 3 | 1.2 | 27 | 0.21 |
| Example 2 | 43 | 16 | 3 | 1.6 | 50 | 0.47 |
| Example 3 | 43 | 16 | 3 | 2.4 | 48 | 0.54 |
| Example 4 | 43 | 16 | 3 | 3.0 | 46 | 0.59 |
| Example 5 | 43 | 16 | 3 | 3.7 | 43 | 0.62 |
| Example 6 | 43 | 16 | 3 | 4.6 | 43 | 0.69 |
| Comparative Example 1 | 43 | 16 | 3 | 6.9 | 37 | 0.71 |
| Comparative Example 2 | 43 | 16 | 3 | 1.1 | 107 | 0.81 |
| Comparative Example 3 | 43 | 16 | — | 1.0 | — | — |
| Comparative Example 4 | 43 | 16 | 3 | 1.0 | — | — |

TABLE 2

| | Circle Equivalent Diameter of Fiber Cross-Section μm | Average Pore Radius nm | Pore Distribution Index — | Pore Specific Surface Area m²/g | Index of Pore Shape (Dxv) — | Surface Pore Ratio % | Dense Layer Thickness in Near-Surface Region μm | Adsorbed Amount of β2-MG (per surface area) μg/cm² | Adsorbed Amount of β2-MG (per volume) mg/cm³ |
|---|---|---|---|---|---|---|---|---|---|
| Example 1 | 140 | — | — | (≥250) | 1.0 | 3.8 | 0.75 | 0.095 | 0.033 |
| Example 2 | 140 | — | — | (≥250) | 1.1 | 3.7 | 0.71 | 0.096 | 0.035 |
| Example 3 | 140 | 6.6 | 1.19 | 311 | 1.0 | 3.8 | 0.71 | 0.095 | 0.038 |
| Example 4 | 140 | — | — | (≥250) | 1.0 | 3.7 | 0.74 | 0.094 | 0.040 |
| Example 5 | 140 | — | — | (≥250) | 1.0 | 3.2 | 0.83 | 0.081 | 0.037 |
| Example 6 | 140 | — | — | (≥250) | 1.1 | 2.8 | 0.99 | 0.065 | 0.032 |
| Comparative Example 1 | 140 | — | — | (≥250) | 1.0 | 1.7 | 1.63 | 0.019 | 0.011 |
| Comparative Example 2 | 140 | — | — | (≥250) | 1.0 | 3.6 | 0.77 | 0.095 | 0.029 |
| Comparative Example 3 | 140 | — | — | (≥250) | 1.0 | 3.7 | 0.72 | 0.096 | 0.027 |
| Comparative Example 4 | 140 | — | — | (≥250) | 1.0 | 3.1 | 0.89 | 0.085 | 0.024 |

Example 7

Fibers were prepared under the same conditions as in Example 1 except for using a spinneret having a configuration shown in FIG. 5 and having a discharge opening with dimensions shown in Table 3. The results are shown in Tables 3 and 4.

Example 8

Fibers were prepared under the same conditions as in Example 1 except for using a spinneret having a configuration shown in FIG. 5 and having a discharge opening with dimensions shown in Table 3. The results are shown in Tables 3 and 4.

Example 9

Fibers were prepared under the same conditions as in Example 1 except for using a spinneret having a configuration shown in FIG. 5 and having a discharge opening with dimensions shown in Table 3. The results are shown in Tables 3 and 4.

Example 10

Fibers were prepared under the same conditions as in Example 1 except for using a spinneret having a configuration shown in FIG. 5 and having a discharge opening with dimensions shown in Table 3. The results are shown in Tables 3 and 4. In addition, the results of Example 3 are also shown in Tables 3 and 4 for comparison.

TABLE 3

| | Configuration/Dimension of Spinneret | | | | | | | | |
|---|---|---|---|---|---|---|---|---|---|
| | Spinneret Configuration (Drawing No.) | D (mm) | W (mm) | L (mm) | L/W | d (mm) | Discharge Amount cc/min | Transit Time in Dry Part sec | Cool Air Velocity m/s |
| Example 7 | FIG. 5 | 0.20 | 0.10 | 1.0 | 10.0 | 0.10 | 1.1 | 1.42 | 2.5 |
| Example 3 | FIG. 5 | 0.20 | 0.10 | 1.0 | 10.0 | 0.25 | 1.1 | 1.42 | 2.5 |
| Example 8 | FIG. 5 | 0.20 | 0.10 | 1.0 | 10.0 | 0.30 | 1.1 | 1.42 | 2.5 |
| Example 9 | FIG. 5 | 0.20 | 0.10 | 1.0 | 10.0 | 0.40 | 1.1 | 1.42 | 2.5 |
| Example 10 | FIG. 5 | 0.20 | 0.10 | 1.0 | 10.0 | 0.60 | 1.1 | 1.42 | 2.5 |

| | Temperature of Coagulating Bath °C. | Taken-up Speed m/min | Number of Projected Parts | Modification Degree Do/Di — | Projected Part Width ω μm | Projected Part Form Exponent ω/Di — |
|---|---|---|---|---|---|---|
| Example 7 | 43 | 16 | 3 | 2.3 | 9 | 0.09 |
| Example 3 | 43 | 16 | 3 | 2.4 | 48 | 0.54 |
| Example 8 | 43 | 16 | 3 | 2.4 | 73 | 0.89 |
| Example 9 | 43 | 16 | 3 | 2.4 | 94 | 1.22 |
| Example 10 | 43 | 16 | 3 | 2.2 | 102 | 1.40 |

TABLE 4

| | Circle Equivalent Diameter of Fiber Cross-Section μm | Average Pore Radius nm | Pore Distribution Index — | Pore Size Specific Surface Area m²/g | Index of Pore Shape (Dxv) — | Surface Pore Ratio % | Dense Layer Thickness in Near-Surface Region μm | Adsorbed Amount of $\beta_2$-MG (per surface area) μg/cm² | (per volume) mg/cm³ |
|---|---|---|---|---|---|---|---|---|---|
| Example 7 | 140 | — | — | (≥250) | 1.0 | 3.7 | 0.70 | 0.095 | 0.038 |
| Example 3 | 140 | 6.6 | 1.19 | 311 | 1.0 | 3.8 | 0.71 | 0.095 | 0.038 |
| Example 8 | 140 | — | — | (≥250) | 1.0 | 3.5 | 0.75 | 0.088 | 0.035 |
| Example 9 | 140 | — | — | (≥250) | 1.1 | 3.4 | 0.82 | 0.083 | 0.033 |
| Example 10 | 140 | — | — | (≥250) | 1.0 | 2.9 | 1.10 | 0.075 | 0.029 |

Example 11

Fibers were prepared under the same conditions as in Example 1 except that a spinneret having a configuration shown in FIG. 5 and having a discharge opening with dimensions shown in Table 5 was used and a discharge amount of a raw solution was changed to 0.71 g. The results are shown in Tables 5 and 6.

Example 12

Fibers were prepared under the same conditions as in Example 1 except that a spinneret having a configuration shown in FIG. 5 and having a discharge opening with dimensions shown in Table 5 was used and a discharge amount of a raw solution was changed to 1.6 g. The results are shown in Tables 5 and 6.

Example 13

Fibers were prepared under the same conditions as in Example 1 except that a spinneret having a configuration shown in FIG. 5 and having a discharge opening with dimensions shown in Table 5 was used and a discharge amount of a raw solution was changed to 2.1 g. The results are shown in Tables 5 and 6. In addition, the results of Example 3 are also shown in Tables 5 and 6 for comparison.

TABLE 5

| | Configuration/Dimension of Spinneret | | | | | | | | |
|---|---|---|---|---|---|---|---|---|---|
| | Spinneret Configuration (Drawing No.) | D (mm) | W (mm) | L (mm) | L/W | d (mm) | Discharge Amount cc/min | Transit Time in Dry Part sec | Cool Air Velocity m/s |
| Example 11 | FIG. 5 | 0.20 | 0.10 | 1.0 | 10.0 | 0.25 | 0.71 | 1.42 | 1.9 |
| Example 3 | FIG. 5 | 0.20 | 0.10 | 1.0 | 10.0 | 0.25 | 1.1 | 1.42 | 2.5 |
| Example 12 | FIG. 5 | 0.20 | 0.10 | 1.0 | 10.0 | 0.25 | 1.6 | 1.42 | 3.4 |
| Example 13 | FIG. 5 | 0.20 | 0.10 | 1.0 | 10.0 | 0.25 | 2.1 | 1.42 | 4.9 |

| | Temperature of Coagulating Bath °C. | Taken-up Speed m/min | Number of Projected Parts | Modification Degree Do/Di — | Projected Part Width ω μm | Projected Part Form Exponent ω/Di — |
|---|---|---|---|---|---|---|
| Example 11 | 43 | 16 | 3 | 2.3 | 28 | 0.47 |
| Example 3 | 43 | 16 | 3 | 2.4 | 48 | 0.54 |
| Example 12 | 43 | 16 | 3 | 2.4 | 54 | 0.47 |
| Example 13 | 43 | 16 | 3 | 2.3 | 64 | 0.47 |

TABLE 6

| | Circle Equivalent Diameter of Fiber Cross-Section μm | Average Pore Radius nm | Pore Distribution Index — | Pore Size Specific Surface Area m²/g | Index of Pore Shape (Dxv) — | Surface Pore Ratio % | Dense Layer Thickness in Near-Surface Region μm | Adsorbed Amount of $\beta_2$-MG (per surface area) μg/cm² | (per volume) mg/cm³ |
|---|---|---|---|---|---|---|---|---|---|
| Example 11 | 88 | — | — | (≥250) | 1.0 | 4.1 | 0.69 | 0.099 | 0.062 |
| Example 3 | 140 | 6.6 | 1.19 | 311 | 1.0 | 3.8 | 0.71 | 0.095 | 0.038 |
| Example 12 | 182 | — | — | (≥250) | 1.0 | 3.6 | 0.79 | 0.090 | 0.028 |
| Example 13 | 201 | — | — | (≥250) | 1.1 | 2.8 | 1.20 | 0.073 | 0.020 |

Example 14

Fibers were prepared under the same conditions as in Example 1 except for using a spinneret having a configuration shown in FIG. 6 and having a discharge opening with dimensions shown in Table 7. The results are shown in Tables 7 and 8.

Example 15

Fibers were prepared under the same conditions as in Example 1 except for using a spinneret having a configuration shown in FIG. 7 and having a discharge opening with dimensions shown in Table 7. The results are shown in Tables 7 and 8.

Example 16

Fibers were prepared under the same conditions as in Example 1 except for using a spinneret having a configuration shown in FIG. 8 and having a discharge opening with dimensions shown in Table 7. The results are shown in Tables 7 and 8. In addition, the results of Example 3 are also shown in Tables 7 and 8 for comparison.

Example 17

Fibers were prepared under the same conditions as in Example 1 except that a spinneret having a configuration shown in FIG. 6 and having a discharge opening with dimensions shown in Table 9 was used and a transit time in the dry part was set to 0.75 second. The results are shown in Tables 9 and 10.

Example 18

Fibers were prepared under the same conditions as in Example 1 except that a spinneret having a configuration shown in FIG. 6 and having a discharge opening with dimensions shown in Table 9 was used and a transit time in the dry part was set to 0.375 second. The results are shown in Tables 9 and 10.

Comparative Example 5

Fibers were prepared under the same conditions as in Example 1 except that a spinneret having a configuration shown in FIG. 6 and having a discharge opening with dimensions shown in Table 9 was used and a transit time in the dry part was set to 0.034 second. The results are shown in Tables 9 and 10.

Comparative Example 6

Fibers were prepared under the same conditions as in Example 1 except that a spinneret having a configuration shown in FIG. 6 and having a discharge opening with dimensions shown in Table 9 was used and a transit time in the dry part was set to 0.019 second. The results are shown in Tables 9 and 10. In addition, the results of Example 14 are also shown in Tables 9 and 10 for comparison.

TABLE 7

| | Configuration/Dimension of Spinneret | | | | | | | | |
|---|---|---|---|---|---|---|---|---|---|
| | Spinneret Configuration (Drawing No.) | D (mm) | W (mm) | L (mm) | L/W | d (mm) | Discharge Amount cc/min | Transit Time in Dry Part sec | Cool Air Velocity m/s |
| Example 3 | FIG. 5 | 0.20 | 0.10 | 1.0 | 10.0 | 0.25 | 1.1 | 1.42 | 2.5 |
| Example 14 | FIG. 6 | 0.20 | 0.10 | 1.0 | 10.0 | 0.25 | 1.1 | 1.42 | 2.5 |
| Example 15 | FIG. 7 | 0.20 | 0.10 | 1.0 | 10.0 | 0.25 | 1.1 | 1.42 | 2.5 |
| Example 16 | FIG. 8 | 0.20 | 0.10 | 1.0 | 10.0 | 0.25 | 1.1 | 1.42 | 2.5 |

| | Temperature of Coagulating Bath °C. | Taken-up Speed m/min | Number of Projected Parts | Modification Degree $D_o/D_i$ — | Projected Part Width $\omega$ μm | Projected Part Form Exponent $\omega/D_i$ — |
|---|---|---|---|---|---|---|
| Example 3 | 43 | 16 | 3 | 2.4 | 48 | 0.54 |
| Example 14 | 43 | 16 | 4 | 2.1 | 36 | 0.43 |
| Example 15 | 43 | 16 | 5 | 1.5 | 32 | 0.39 |
| Example 16 | 43 | 16 | 6 | 1.5 | 28 | 0.36 |

TABLE 8

| | Circle Equivalent Diameter of Fiber Cross-Section μm | Average Pore Radius nm | Pore Size Distribution Index — | Pore Specific Surface Area m²/g | Index of Pore Shape (Dxv) — | Surface Pore Ratio % | Dense Layer Thickness in Near-Surface Region μm | Adsorbed Amount of $\beta_2$-MG (per surface area) μg/cm² | (per volume) mg/cm³ |
|---|---|---|---|---|---|---|---|---|---|
| Example 3 | 140 | 6.6 | 1.19 | 311 | 1.0 | 3.8 | 0.71 | 0.095 | 0.038 |
| Example 14 | 140 | — | — | (≥250) | 1.0 | 3.8 | 0.76 | 0.102 | 0.046 |
| Example 15 | 140 | — | — | (≥250) | 1.1 | 3.6 | 0.79 | 0.105 | 0.051 |
| Example 16 | 140 | — | — | (≥250) | 1.2 | 3.5 | 0.81 | 0.099 | 0.048 |

TABLE 9

| | Configuration/Dimension of Spinneret | | | | | | | |
|---|---|---|---|---|---|---|---|---|
| | Spinneret Configuration (Drawing No.) | D (mm) | W (mm) | L (mm) | L/W | d (mm) | Discharge Amount cc/min | Transit Time in Dry Part sec | Cool Air Velocity m/s |
| Example 14 | FIG. 6 | 0.20 | 0.10 | 1.0 | 10.0 | 0.25 | 1.1 | 1.42 | 2.5 |
| Example 17 | FIG. 6 | 0.20 | 0.10 | 1.0 | 10.0 | 0.25 | 1.1 | 0.75 | 2.5 |
| Example 18 | FIG. 6 | 0.20 | 0.10 | 1.0 | 10.0 | 0.25 | 1.1 | 0.375 | 2.5 |
| Comparative Example 5 | FIG. 6 | 0.20 | 0.10 | 1.0 | 10.0 | 0.25 | 1.1 | 0.034 | 2.5 |
| Comparative Example 6 | FIG. 6 | 0.20 | 0.10 | 1.0 | 10.0 | 0.25 | 1.1 | 0.019 | 2.5 |

| | Temperature of Coagulating Bath °C. | Taken-up Speed m/min | Number of Projected Parts | Modification Degree Do/Di — | Projected Part Width ω μm | Projected Part Form Exponent ω/Di — |
|---|---|---|---|---|---|---|
| Example 14 | 43 | 16 | 4 | 2.1 | 36 | 0.43 |
| Example 17 | 43 | 16 | 4 | 2.1 | 37 | 0.43 |
| Example 18 | 43 | 16 | 4 | 2.1 | 38 | 0.43 |
| Comparative Example 5 | 43 | 16 | 4 | 2.2 | 39 | 0.43 |
| Comparative Example 6 | 43 | 16 | 4 | 2.5 | 38 | 0.43 |

TABLE 10

| | Circle Equivalent Diameter of Fiber Cross-Section μm | Average Pore Radius nm | Pore Size Distribution Index — | Specific Surface Area m²/g | Pore Shape (Dxv) — | Index of Surface Pore Ratio % | Dense Layer Thickness in Near-Surface Region μm | Adsorbed Amount of $β_2$-MG (per surface area) μg/cm² | (per volume) mg/cm³ |
|---|---|---|---|---|---|---|---|---|---|
| Example 14 | 140 | 6.8 | 1.25 | 299 | 1.0 | 3.8 | 0.76 | 0.102 | 0.046 |
| Example 17 | 140 | — | — | (≥250) | 1.0 | 3.3 | 0.91 | 0.090 | 0.040 |
| Example 18 | 140 | — | — | (≥250) | 1.1 | 2.8 | 1.30 | 0.060 | 0.027 |
| Comparative Example 5 | 140 | — | — | (≥250) | 1.0 | 0.9 | 2.20 | 0.013 | 0.006 |
| Comparative Example 6 | 140 | — | — | (≥250) | 1.1 | 0.4 | 4.00 | 0.005 | 0.002 |

Example 19

Fibers were prepared under the same conditions as in Example 1 except that a spinneret having a configuration shown in FIG. 6 and having a discharge opening with dimensions shown in Table 11 was used and a temperature of coagulating bath was changed to 85° C. The results are shown in Tables 11 and 12.

Example 20

Fibers were prepared under the same conditions as in Example 1 except that a spinneret having a configuration shown in FIG. 6 and having a discharge opening with dimensions shown in Table 11 was used and a temperature of coagulating bath was changed to 60° C. The results are shown in Tables 11 and 12.

Example 21

Fibers were prepared under the same conditions as in Example 1 except that a spinneret having a configuration shown in FIG. 6 and having a discharge opening with dimensions shown in Table 11 was used and a temperature of coagulating bath was changed to 30° C. The results are shown in Tables 11 and 12.

Example 22

Fibers were prepared under the same conditions as in Example 1 except that a spinneret having a configuration shown in FIG. 6 and having a discharge opening with dimensions shown in Table 11 was used and a temperature of coagulating bath was changed to 20° C. The results are shown in Tables 11 and 12.

Example 23

Fibers were prepared under the same conditions as in Example 1 except that a spinneret having a configuration shown in FIG. 6 and having a discharge opening with dimensions shown in Table 11 was used and a temperature of coagulating bath was changed to 10° C. The results are shown in Tables 11 and 12. In addition, the results of Example 14 are also shown in Tables 11 and 12 for comparison.

TABLE 11

| | Configuration/Dimension of Spinneret | | | | | | | |
|---|---|---|---|---|---|---|---|---|
| | Spinneret Configuration (Drawing No.) | D (mm) | W (mm) | L (mm) | L/W | d (mm) | Discharge Amount cc/min | Transit Time in Dry Part sec | Cool Air Velocity m/s |
| Example 19 | FIG. 6 | 0.20 | 0.10 | 1.0 | 10.0 | 0.25 | 1.1 | 1.42 | 2.5 |
| Example 20 | FIG. 6 | 0.20 | 0.10 | 1.0 | 10.0 | 0.25 | 1.1 | 1.42 | 2.5 |
| Example 14 | FIG. 6 | 0.20 | 0.10 | 1.0 | 10.0 | 0.25 | 1.1 | 1.42 | 2.5 |
| Example 21 | FIG. 6 | 0.20 | 0.10 | 1.0 | 10.0 | 0.25 | 1.1 | 1.42 | 2.5 |
| Example 22 | FIG. 6 | 0.20 | 0.10 | 1.0 | 10.0 | 0.25 | 1.1 | 1.42 | 2.5 |
| Example 23 | FIG. 6 | 0.20 | 0.10 | 1.0 | 10.0 | 0.25 | 1.1 | 1.42 | 2.5 |

| | Temperature of Coagulating Bath ° C. | Taken-up Speed m/min | Number of Projected Parts | Modification Degree Do/Di — | Projected Part Width ω μm | Projected Part Form Exponent ω/Di — |
|---|---|---|---|---|---|---|
| Example 19 | 85 | 16 | 4 | 1.8 | 48 | 0.43 |
| Example 20 | 60 | 16 | 4 | 2.0 | 43 | 0.43 |
| Example 14 | 43 | 16 | 4 | 2.1 | 36 | 0.43 |
| Example 21 | 30 | 16 | 4 | 2.3 | 34 | 0.43 |
| Example 22 | 20 | 16 | 4 | 2.3 | 33 | 0.43 |
| Example 23 | 10 | 16 | 4 | 2.8 | 28 | 0.43 |

TABLE 12

| | Circle Equivalent Diameter of Fiber Cross-Section μm | Average Pore Radius nm | Pore Size Distribution Index — | Pore Specific Surface Area m²/g | Index of Pore Shape Dxv — | Surface Pore Ratio % | Dense Layer Thickness in Near-Surface Region μm | Adsorbed Amount of $\beta_2$-MG (per surface area) μg/cm² | (per volume) mg/cm³ |
|---|---|---|---|---|---|---|---|---|---|
| Example 19 | 150 | 11.4 | 1.97 | 127 | 1.0 | 3.7 | 0.81 | 0.089 | 0.034 |
| Example 20 | 150 | 8.9 | 1.36 | 226 | 1.1 | 3.7 | 0.79 | 0.099 | 0.038 |
| Example 14 | 140 | 6.8 | 1.25 | 299 | 1.0 | 3.8 | 0.75 | 0.102 | 0.046 |
| Example 21 | 132 | 5.1 | 1.17 | 354 | 1.1 | 3.8 | 0.78 | 0.101 | 0.050 |
| Example 22 | 123 | 3.2 | 1.08 | 429 | 1.0 | 3.6 | 0.75 | 0.100 | 0.054 |
| Example 23 | 109 | 0.8 | 0.96 | 505 | 1.1 | 3.5 | 0.75 | 0.059 | 0.041 |

Example 24

[Preparation of Column]

The porous fibers with a Y-shaped cross section obtained in Example 3 were bundled with use of a publicly known method and incorporated into a polycarbonate cylindrical casing having an inner diameter of 56 mm and an axial length of 58 mm in the straight form so that a packing ratio of the fibers is 53%. Next, polypropylene mesh filters which were cut to a size having a diameter equal to a casing inner diameter and have an opening of a circle equivalent diameter of 84 μm and an aperture ratio of 36%, were fitted to the inlet/outlet of the fluid that is to be treated at both end surfaces of the column. Finally, caps referred to as a header which have the inlet or the outlet of the fluid that is to be treated, were attached to casing ends.

[Measurement of Adsorption Performance of Column]

As an evaluation of the adsorption performance of the column, a clearance of $\beta_2$-MG was measured. It is known that $\beta_2$-MG is a pathogenic protein of dialysis-related amyloidosis of complicating disease of long-term dialysis. Blood plasma was obtained from cattle blood to which disodium ethylenediaminetetraacetate is added by centrifugal separation. The blood plasma was adjusted so that an amount of total protein is 6.5±0.5 g/dL. In addition, as a bovine blood plasma, one within 5 days after blood draw was used. Next, the bovine blood plasma $\beta_2$-MG was added so as to have a concentration of 1 mg/L and the resulting mixture was stirred. Such bovine blood plasma was separated into 2 L for circulation and 1.5 L for clearance measurement.

A circuit was set as in FIG. 10. Of the circuit, an inlet part from which the fluid that is to be treated was taken in was denoted by Bi, and a fluid outlet part after passing the fluid through the purification column was denoted by Bo.

Bi was put in a beaker for circulation in which 2 L of the bovine blood plasma (37° C.) adjusted above had been put, and the resulting mixture was discharged at a flow rate of 200 mL/min by starting a pump, and immediately after 90 seconds of the fluid to be discharged from the Bo was disposed, Bo was put in a beaker for circulation to bring the fluid into circulation. After the fluid was circulated for 1 hour, the pump was stopped.

Next, the Bi was put in the bovine blood plasma for clearance measurement adjusted above, and Bo was put in the beaker for disposal. A flow rate was set to 200 mL/min, and 10 mL of a sample was taken from the bovine blood plasma (37° C.) for clearance measurement after a lapse of two minutes from the start of a pump and referred to as a Bi fluid. After a lapse of four minutes 30 seconds from the start of the pump, 10 mL of a sample flown from the Bo was taken and referred to as a Bo fluid. These samples were stored in a freezer at −20° C. or lower.

A clearance was calculated by the following formula I from a $\beta_2$-MG concentration of each fluid. Since there may be cases where measurements are different depending on lots of the cattle blood, the bovine blood plasma of the same lot was used for all of Examples and Comparative Examples.

$$Co(\text{ml/min}) = (CBi - CBo) \times Q_B / CBi \quad (I)$$

In the formula I, $C_o = \beta_2$-MG clearance (ml/min), $CBi = \beta_2$-MG concentration in the fluid Bi, $CBo = \beta_2$-MG concentration in the fluid Bo, $Q_B$ = Bi pump flow rate (ml/min). The results are shown in Table 13.

Example 25

The porous fibers with a Y-shaped cross section obtained in Example 3 and the porous fibers with a circular cross section obtained in Comparative Example 3 were mixed in a ratio of 9:1 and bundled to form a fiber bundle in which a ratio of the porous fibers with a Y-shaped cross section was 90%, and using the fiber bundle, a column was prepared by the same method as in Example 24. The adsorption performance of the column was measured by the same technique as in Example 24. The results are shown in Table 13.

Example 26

The porous fibers with a Y-shaped cross section obtained in Example 3 and the porous fibers with a circular cross section obtained in Comparative Example 3 were mixed in a ratio of 5:1 and bundled to form a fiber bundle in which a ratio of the porous fibers with a Y-shaped cross section was 83%, and using the fiber bundle, a column was prepared by the same method as in Example 24. The adsorption performance of the column was measured by the same technique as in Example 24. The results are shown in Table 13.

Example 27

The porous fibers with a Y-shaped cross section obtained in Example 3 and the porous fibers with a circular cross section obtained in Comparative Example 3 were mixed in a ratio of 2:1 and bundled to form a fiber bundle in which a ratio of the porous fibers with a Y-shaped cross section was 67%, and using the fiber bundle, a column was prepared by the same method as in Example 24. The adsorption performance of the column was measured by the same technique as in Example 24. The results are shown in Table 13.

Example 28

The porous fibers with a Y-shaped cross section obtained in Example 3 and the porous fibers with a circular cross section obtained in Comparative Example 3 were mixed in a ratio of 1:1 and bundled to form a fiber bundle in which a ratio of the porous fibers with a Y-shaped cross section was 50%, and using the fiber bundle, a column was prepared by the same method as in Example 24. The adsorption performance of the column was measured by the same technique as in Example 24. The results are shown in Table 13.

Example 29

The porous fibers with a Y-shaped cross section obtained in Example 3 and the porous fibers with a circular cross section obtained in Comparative Example 3 were mixed in a ratio of 1:2 and bundled to form a fiber bundle in which a ratio of the porous fibers with a Y-shaped cross section was 33%, and using the fiber bundle, a column was prepared by the same method as in Example 24. The adsorption performance of the column was measured by the same technique as in Example 24. The results are shown in Table 13.

Comparative Example 7

[Preparation of Column]
The porous fibers with a circular cross section obtained in Comparative Example 3 were bundled with use of a publicly known method and incorporated into a polycarbonate cylindrical casing having an inner diameter of 56 mm and an axial, length of 58 mm in the straight form so that a packing ratio of the fibers is 53%. Next, polypropylene mesh filters which were cut to a size having a diameter equal to a casing inner diameter and have an opening of a circle equivalent diameter of 84 μm and an aperture ratio of 36%, were fitted to the inlet/outlet of the fluid that is to be treated at both end surfaces of the column. Finally, caps referred to as a header which have the inlet or the outlet of the fluid that is to be treated, were attached to casing ends.
[Measurement of Adsorption Performance of Column]
The adsorption performance of the column was measured by the same technique as in Example 24. The results are shown in Table 13.

Comparative Example 8

The porous fibers with a Y-shaped cross section obtained in Example 3 and the porous fibers with a circular cross section obtained in Comparative Example 3 were mixed in a ratio of 1:9 and bundled to form a fiber bundle in which a ratio of the porous fibers with a Y-shaped cross section was 17%, and using the fiber bundle, a column was prepared by the same method as in Comparative Example 7. The adsorption performance of the column was measured by the same technique as in Example 24. The results are shown in Table 13.

TABLE 13

| | Ratio of Porous Fibers with Y-shaped Cross Section in Fiber Bundle (%) | β2-MG Clearance (ml/min) |
|---|---|---|
| Example 24 | 100 | 68 |
| Comparative Example 7 | 0 | 49 |
| Example 25 | 90 | 67 |
| Example 26 | 83 | 64 |
| Example 27 | 67 | 61 |
| Example 28 | 50 | 57 |
| Example 29 | 33 | 54 |
| Comparative Example 8 | 17 | 50 |

Examples 1 to 6 are experiments in which the modification degree was varied, and it is found from Tables 1 and 2 show that the adsorption performance per volume is improved as the modification degree increases; however, the adsorption performance has a local maximum point and turns to decline in the modification degree of a certain value or more. When the modification degree is excessively as high as 6.9 like Comparative Example 1, performance per surface area is deteriorated, and therefore performance per volume is deteriorated by a large amount. A reduction of the surface pore ratio is thought to be the cause of this. Specifically, it is supposed that since the projected part is long, cooling during spinning becomes uneven and there may be a location without being adequately blown with a cool wind. Thus, the modification degree is preferably 6.6 or less. In Comparative Example 2, since the tip circle diameter d of the spinneret configuration was small, the modification degree was reduced resulting in low adsorption performance. Comparative Example 3 shows the results of the so-called circular fiber not having the projected part. It is found that in the circular fiber, since the surface area per volume is minimum, the adsorbed amount per volume is limited. Comparative Example 4 shows the results of spinning using the spinneret having a shape almost similar to the desired fiber cross section shape. The resulting fiber is circular, and did not achieve a desired modification degree. The reason for this is that the d does not exist in the spinneret and the L/W is also as low as 2.7. Further, draw resonance was generated because of a large area of a discharge opening of the spinneret, and spinning became unstable.

Examples 3 and 7 to 10 are experiments in which the projected part width and the projected part font exponent were varied, and Tables 3 and 4 show that the adsorbed amount per surface area tends to be reduced when the projected part width and the projected part form exponent form are certain values or more. The reason for this is supposedly that cooling efficiency during spinning is reduced because of an increase of a volume of a projected part portion resulting in a reduction of the surface pore ratio and an increase in a thickness of a dense layer in the surface.

It is found from Tables 5 and 6 that when a circle equivalent diameter of a fiber cross section which is a volume of a fiber itself is increased, the adsorbed amount per surface area tends to be reduced. The reason for this is also supposedly that cooling efficiency during spinning is reduced because of an increase of a volume of a projected part portion.

Tables 7 and 8 show the results of increasing the number of projected parts to 3 to 6. It is found that the modification degree increases and the adsorbed amount per volume is increased as the number of projected parts increases.

From Tables 9 and 10, Examples 14, 17 and 18, and Comparative Examples 5 and 6 show the results of varying a dry length, more specifically changing a transit time in the dry part. It is found from these results that when the transit time in the dry part is set to 0.034 second or less, an increase in thickness of the dense layer and a significant reduction of the pore ratio occur, resulting in a large reduction of the adsorbed amount per surface area.

From Tables 11 and 12, Examples 14, and 19 to 23 show the results of varying a temperature of coagulating bath, an average pore radius, a pore size distribution index, and a pore specific surface area. It is found that the adsorption performance is improved as the pore specific surface area is increased. However, in Example 23 in which the average pore radius is 0.8 nm, the adsorbed amounts per surface area and per volume are slightly reduced. The reason for this is supposedly that the pore size was too small to a size of $\beta_2$-MG. In addition, pore specific surface areas of Examples 1 to 18 were not measured, but these can be predicted to be 250 m$^2$/g or more since the coagulating bath temperature was 43° C. in any case.

Example 24 and Comparative Example 7 described in Table 13 show the results of preparing the column and evaluating the adsorption performance. In Example 24 in which the porous fibers with the modified cross section was incorporated, the performance tends to be higher than that of Comparative Example 7 in which the fiber has a circular cross section. Examples 25 to 29, and Comparative Example 8 show the results of varying a ratio of the porous fibers with a Y-shaped cross section in the fiber bundle in a column from 17 to 90%. The adsorption performance tends to be improved as the ratio of the porous fibers with a Y-shaped cross section is increased, but the clearance at the time when the ratio is 17% is almost equal to that of Comparative Example 7 in which the ratio is 0%, and the effect according to the present invention was not so found.

DESCRIPTION OF REFERENCE SIGNS

1: Circumscribed circle
2: Inscribed circle
3: Diameter of a circumscribed circle Do
4: Diameter of an inscribed circle Di
5: Concentric circles passing points which divides a line segment of radius into five equal lengths
6: Central part region
7: near-outer surface region
8: Center of an inscribed circle
9: Tip portion of a projected part
10: Point at which a straight line connecting between a center of an inscribed circle and a tip portion of a projected part, and the inscribed circle intersect.
11: Projected part width ω
12: Central circle
13: Width of a slit portion
14: Length of a slit portion
15: Diameter of a tip circle
16: Purification column
17: Pump
18: Warm water bath of 37° C.
19: Beaker for disposal
20: Blood plasma for circulation
21: Blood plasma for clearance measurement

The invention claimed is:

1. The porous fibers satisfying the following conditions (a), (b) and (c) and having a shape in which three or more projected parts are continuously present in the lengthwise direction on the periphery part of a solid-state fiber:
  (a) when the diameter of an inscribed circle is denoted by Di and the diameter of a circumscribed circle is denoted by Do in a cross section,
    a modification degree Do/Di is 1.2 to 6.6, and
  (b) the specific surface area of pores is 50 m$^2$/g or more, and
  (c) surface pore ratio is 30% or less.

2. The porous fibers according to claim 1, wherein when an average of widths of all projected parts in the cross section is denoted by ω, ω/Di is 0.05 to 2.0.

3. The porous fibers according to claim 1, wherein the average of widths of all projected parts in the cross section ω is 200 μm or less.

4. The porous fibers according to claim 1, wherein the porous fibers have a homogeneous structure in a direction of a cross section.

5. The porous fibers according to claim 1, wherein an average pore radius is 0.5 nm or more and 100 nm or less.

6. The porous fibers according to claim 1, wherein a pore size distribution index is 1.0 or more and 2.8 or less.

7. The porous fibers according to claim 1, wherein a surface pore ratio is 0.5% or more and 30% or less.

8. The porous fibers according to claim 1, wherein a dense layer thickness in the near-surface region of a fiber is 0.01 μm or more.

9. The porous fibers according to claim 1, wherein a dense layer thickness in the near-surface region of a fiber is 3.90 μm or less.

10. The porous fibers according to claim 1, wherein an index of pore shape Dxy is 0.2 or more and 6.0 or less.

11. The porous fibers according to claim 1, wherein a circle equivalent diameter of a cross section is 10 µm or more and less than 300 µm.

12. The porous fibers according to claim 1, wherein the porous fibers contain an amorphous polymer material.

13. The porous fibers according to claim 12, wherein the amorphous polymer material is an ester group-containing polymer.

14. An adsorbent material formed by using the porous fibers according to claim 1 as a bundle including the fibers in a ratio of 18% or more.

15. The adsorbent material according to claim 14 which is for medical care application.

16. The adsorbent material for medical care application according to claim 15, wherein an adsorbed amount of $\beta_2$-microglobulin is 0.005 mg/cm$^3$ or more.

17. A purification column which is formed by arranging the adsorbent material according to claim 14 in the straight form in a direction of a case axis in a plastic casing and attaching an inlet port and an outlet port of the fluid that is to be treated to both ends of the casing.

* * * * *